United States Patent [19]
Eyal et al.

[11] Patent Number: 5,710,028
[45] Date of Patent: Jan. 20, 1998

[54] METHOD OF QUICK SCREENING AND IDENTIFICATION OF SPECIFIC DNA SEQUENCES BY SINGLE NUCLEOTIDE PRIMER EXTENSION AND KITS THEREFOR

[76] Inventors: Nurit Eyal, 7 Keren Kayemet, 76345 Rehovot; Nir Navot, 1 Hapaamon, Neve Afek, 40800 Rosh Haayin, both of Israel

[21] Appl. No.: 317,432

[22] Filed: Oct. 4, 1994

Related U.S. Application Data

[63] Continuation-in-part of Ser. No. 84,505, Jul. 1, 1993, abandoned, which is a continuation-in-part of Ser. No. 919,872, Jul. 27, 1992, abandoned.

[30] Foreign Application Priority Data

Jul. 2, 1992 [IL] Israel .................................. 102382

[51] Int. Cl.$^6$ .................. C12P 19/34; C12Q 1/68; C07H 21/04; C07H 21/02
[52] U.S. Cl. .................. 435/91.1; 435/6; 536/24.33; 536/26.66; 935/77; 935/78
[58] Field of Search .................. 435/6, 91.1; 935/77, 935/78; 536/24.33, 26.66

[56] References Cited

U.S. PATENT DOCUMENTS 4,072,574  2/1978  Loeb et al. .................. 195/103.5

(List continued on next page.)

FOREIGN PATENT DOCUMENTS 0 063 879  3/1982  European Pat. Off. .

(List continued on next page.)

OTHER PUBLICATIONS

Alberts, B. et al, "Molecular Biology of the Cell", 2nd Ed., pp. 38, 42, 46–57.

(List continued on next page.)

*Primary Examiner*—W. Gary Jones
*Assistant Examiner*—Paul B. Tran
*Attorney, Agent, or Firm*—Mark M. Friedman

[57] ABSTRACT

A method of simultaneous determination of the identity of nucleotide bases at specific positions in nucleic acids of interest, which includes (a) treating a sample containing the nucleic acids of interest to obtain unpaired nucleotide bases spanning the specific positions, if the nucleic acids are not already single stranded; (b) contacting the unpaired nucleotide bases with combinations of various marked oligonucleotide primers each for hybridizing with a stretch of nucleotide bases present in each nucleic acid of interest immediately adjacent the nucleotide base to be identified, so as to form a duplex between the primer and the nucleic acid of interest such that the nucleotide base to be identified is the first unpaired base in the template immediately 5' of the nucleotide base annealed with the 3'-end of the primer in the duplex; (c) contacting the duplex with the reagent which includes an aqueous carrier, and at least one primer extension unit, the primer extension unit including an extension moiety a separation moiety and a detection moiety, with the extension moiety for specifically halting a nucleic acid template dependent, primer extension reaction, in a manner which is strictly dependent on the identity of the unpaired nucleotide base of the template immediately adjacent to, and 3' of, the 3'-end of the primer, with the separation moiety permitting the affinity separation of the primer extension unit from unincorporated, or non-extended, primers, and with the detection moiety enabling the direct or indirect detection of the presence of a primer extension unit the contacting taking place under conditions permitting the base pairing of the complementary extension moiety of the primer extension unit present in the reagent with the nucleotide base to be identified and the occurrence of a template dependent, primer extension reaction to incorporate the extension moiety of the primer extension unit at the 3'-end of the primer, resulting in the extension of the primer by a single unit; (d) removing the non-extended marked primer; (e) determining the presence of a nucleotide alteration; and (f) determining the identity of the extended primers, and therefore the kind of alterations and the complete genotype of the examined nucleic acid, by hybridizing the extended primers to complementary oligonucleotides adhered to a test surface.

7 Claims, 10 Drawing Sheets

U.S. PATENT DOCUMENTS

| | | |
|---|---|---|
| 4,863,849 | 9/1989 | Melamede .................................. 435/6 |
| 4,968,602 | 11/1990 | Dattagupta .................................. 435/6 |
| 5,137,806 | 8/1992 | LeMaistre et al. ......................... 435/6 |

FOREIGN PATENT DOCUMENTS

| | | |
|---|---|---|
| WO 90/09455 | 8/1990 | WIPO . |
| WO 91/02087 | 2/1991 | WIPO . |
| WO 91/13075 | 9/1991 | WIPO . |
| WO 92/15712 | 9/1992 | WIPO . |
| WO 93/25563 | 12/1993 | WIPO . |

OTHER PUBLICATIONS

Sanger, F. et al, "DNA Sequencing with Chain–Terminating Inhibitors", Proc. Natl. Acad. Sci. USA vol. 74, No. 12 pp. 5463–5467 (1977).

Maxam, A. et al, "A New Method for Sequencing DNA", Proc. Natl. Acad. Sci. USA vol. 74, No. 12 pp. 560–564 (1977).

Peatie, D., "Direct Chemical Meyhod for Sequencing RNA", Proc. Natl. Acad. Sci. USA vol. 76, No. 4 pp. 1760–1764 (1979).

Kuppuswamy, J. et al, "Single Nucleotide Primer Extension to Detect Genetic Diseases: Experimental Application to Hemophilia B (factor IX) and Systic Fibrosis Genes", Proc. Natl. Acad. Sci. USA vol. 88, pp. 1143–1147 (1991).

Shortle. D. et al, "Gap Misrepair Mutagenesis: Efficient Site–Directed Introduction of Transition, Transversion, and Frameshift Mutations In Vitro", Proc. Natl. Acad. Sci. USA vol. 79, pp. 1588–1592 (1982).

Green, C. et al, "Targeted Deletions of Sequences From Closed Circular DNA", Proc. Natl. Acad. Sci. USA vol. 77, No. 5 pp. 2455–2459 (1980).

Shortle, D. et al, "Segment–Directed Mutagenesis: Construction In Vitro of Point Mutations Limited to a Small Predetermined Region of a Circular DNA Molecule" Proc. Natl. Acad. Sci. USA vol. 77, No. 9 pp. 5375–5379 (1980).

Arbarzua, P. et al, "Enzymatic Techniques for the Isolation of RandomSingle–base Substitutions In Vitro at High Frequency", Proc. Natl. Acad. Sci. USA vol. 81, pp. 2030–2034 (1984).

Lo. K. et al, "Specific Amino Acid Substitutions in Bacterioopsin: Replacement of a Restriction Fragment in the Structural Gene by Synthetic DNA Fragments Containing Altered Codons" Proc. Natl. Acad. Sci. USA vol. 81, pp. 2285–2289 (1984).

Wada, A. et al, "Automatic DNA Sequencer: Computer–Programmed michrochemical manipulator for the Maxam–Gilbert Sequencing Method", Rev. Sci. Instrum 54 (11) pp. 1569–1572 (1993).

Rosenthal, A. et al, "Solid–Phase Methods for Sequencing of Nuceic Acids 1. Simultaneous Sequencing of Different Oligodeoxy ribonucleotides Using a New, Mechanically Stable Anion–Exchange Paper", Nucleic Acid Research, vol. 13 No. 4 pp. 1173–1184 (1985).

Chen, E. et al "Supercoil Sequencing: A Fast and Simple Method for Sequencing Plasmid DNA", DNA, vol. 4, No. 2 pp. 165–170 (1985).

Zimmern, D. et al, "3'–Terminal Nucleotide Sequence of Encephalomyocarditis Virus RNA Determined by Reverse Transcriptase and Chain–Terminating Inhibitors", Proc. Natl. Acad. Sci. USA vol. 75, No. 9 pp. 4257–4261 (1978).

England, et al "3'Terminal Labelling of RNA with T4 RNA Ligase", Nature, vol. 275 pp. 650–561 (1978).

Zoller, M. et al, "Oligonucleotide–Directed Mutagenesis using M13–Derived vectors: An Efficient and General Procedure for the Production of Point Mutations in any Fragment of DNA", Nucleic Acids research, vol. 10 No. 20 pp. 6487–6500 (1982).

Morinaga, Y. et al, "Improvement of Oligonucleotide–Directed Site–Specific Mutagenesis using Double–Stranded Plasmid DNA", Biotechnology, pp. 636–639 (Jul. 1984).

Hunkapiller, M. et al, "A Microchemical Facility for the Analysis and Synthesis of Genes and Proteins", Nature, vol. 310 (Jul. 1984).

Shortle, D. "Directed Mutagenesis" Ann. Rev. Genet. vol. 15 pp. 265–294 (1981).

Matteucci, M.D. et al, "Synthesis of Deoxyoligonucleotides on a Polymer Support" American Chemical Society, (1981).

Botstein, D. et al, "Strategies and Applications of In Vitro Mutagenesis", Science, vol. 229 No. 4719 pp. 1193–1201 (1985).

Sanger, F. et al, "A rapid Method for Determining Sequences in DNA by Primed Synthesis with DNA Polymerase", J. Med. Biol., vol. 94 pp. 441–448 (1975).

Prober, J. et al, "A System for Rapid DNA Sequencing with Fluorescent Chain–Terminating Dideoxnucleotides", Science, pp. 336–341 (Sep. 1987).

Singer–Sam, J. et al, "A Sensitive, Quantitative Assay for Measurement of Allele–Specific Tanscripts Differing by a Single Nucleotide", PRC Methods and Applications, pp. 160–163 (1992).

Hornes, E. et al, "Magnetic DNA Hybridization Properties of Onucleotide Probes Attached to Suoerparamagnetic Beads and Their Use in the Isolation of Poly(A) mRNA From Eukaryotic Cells", GATA, vol. 76 No. 6 pp. 145–150 (1990).

Lee, L., et al, "DNA Sequencing with Dye–Labeled Terminatorsand T7 DNA Polymerase: Effect of Dyes and dNTPs on Incorporation of Dye–Terminators and Probability of Termination Fragments", Nucleic Acids Research, vol. 20 No. 10 pp. 2471–2483 (1992).

Sokolov, B.. "Primer Extension Technique for the Detection of Single Nucleotide in Genomic DNA" Nucleic Acids Research vol. 18 No. 12 p. 3671 (1990).

Zakour, R. et al, "Site Specific Mutagenesis: Insertion of Single Noncomplementary Nucleotides at Specified Sites by Error–Directed DNA Polymerization", Nucleic Acids Research vol. 12 No. 16 pp. 6615–6628 (1984).

Stahl et al., Nuc. Acids Res. 16(7): 3025–3038, 1988.

Carrier of the 409 mutation

Homozygous for the 496 mutation

Fig. 5D

| Nucleotide | Mutations Tested | Patient's Genotype | Fluorescent Units | Pronto™ Pooling results |
|---|---|---|---|---|
| Bio-dATP | IVS2+1 V394L | N/N | 59 | Normal |
| Bio-dATP | IVS2+1 V394L | N370S/N | 46 | Normal |
| Bio-dATP | IVS2+1 V394L | N370S/N370S | 193 | Normal |
| Bio-dATP | IVS2+1 V394L | IVS2+1/N | 2874 | Positive |
| Bio-dATP | IVS2+1 V394I | D409H/D409N | 77 | Normal |
| Bio-dATP | IVS2+1 V394L | L444P/L444P | 277 | Normal |
| Bio-dCTP | 84GG N370S D409H L444P | N/N | 70 | Normal |
| Bio-dCTP | 84GG N370S D409H L444P | N370S/N | 2799 | Positive |
| Bio-dCTP | 84GG N370S D409H L444P | N370S/N370S | 1100 | Positive |
| Bio-dCTP | 84GG N370S D409H L444P | D409H/D409H | 1713 | Positive |
| Bio-dCTP | 84GG N370S D409H L444P | L444P/L444P | 2791 | Positive |

METHOD OF QUICK SCREENING AND IDENTIFICATION OF SPECIFIC DNA SEQUENCES BY SINGLE NUCLEOTIDE PRIMER EXTENSION AND KITS THEREFOR

This is a continuation in part of U.S. patent application Ser. No. 08/084,505, filed Jul. 1, 1993, now abandoned which is a continuation in part of U.S. patent application Ser. No. 07/919,872, filed Jul. 27, 1992, now abandoned.

FIELD AND BACKGROUND OF THE INVENTION

The present invention relates to the quick screening and identification of specific nucleotide sequences and to the detection of mutations and/or polymorphism at particular sites within nucleotide sequences.

More particularly, the present invention concerns a method and kit for quick and simultaneous screening and detection of the presence of certain sequences in a sample or samples of genetic material. The method and kit of the present invention are highly sensitive to small alterations in the sequences examined and may also detect various alterations or sequences, simultaneously. Thus, the method and kit of the present invention are useful in the quick screening of multiple point mutations and/or polymorphism, i.e., single base pair alterations and/or well defined other changes in DNA sequences, derived from different genes, simultaneously.

The present method and kit are also useful for wide screening of populations for specific single base pair alterations in DNA sequences, as well as for wide screening of populations for the presence of foreign genetic material in samples of genetic sequences, e.g., for detecting the presence of specific bacterial or viral nucleotide sequences in human, plant and animal DNA or RNA.

In recent years, following the development of methods such as polymerase chain reaction (PCR), various automated sequencing techniques and a variety of techniques aimed at the identification of sequence alterations, an extremely large number of human genes have been isolated, fully sequenced and the genetic basis of many diseases such as, for example, Cystic Fibrosis, Hemophilia, Lesch-Nyhan syndrome, β-thalassemia, Sickle Cell Anemia, Phenylketonuria, Tay-Sachs, Gaucher, Duehen/Becker muscular dystrophy and many others have been elucidated. A large number of genetic diseases have been shown to be caused by multiple alternative sequence alterations such as a replacement (e.g., point mutation), a deletion or insertion of known number of nucleotides, in the genes of different individuals. For example, 177 different point mutations and 66 different insertions and deletions in the CFTR gene have been identified as alternative genetic origins for this gene associated disease, Cystic Fibrosis (Darvasi, A. and Kerem, B. (1994) Short tandem repeats and mutations in the coding region of human genes, in press). As a consequence of such point mutations or small sequence alterations the protein encoded by such genes is not produced, prematurely truncated or is produced in a modified form which affects its function/s. Much evidence supports the idea that at least part of the variable penetrance, i.e., age of onset and severeness, characterizing some of these diseases is due to the variability of alterations in their associated genes. Furthermore, many cancers have been shown to be associated with somatic point mutations in certain genes.

In view of the aforementioned developments, it is now possible to obtain genetic material from an individual, amplify a certain gene region using PCR technology, and then identify, by DNA sequencing or by other mutation detection approaches, whether the individual has a mutation at any particular site in this region. Furthermore, it is also possible to determine the genotype of such individual, i.e., whether the individual is healthy, has a certain disease or whether the individual is a "carrier" i.e., is heterozygous for the mutation of the site tested. When such analyses are performed on fetal cells, it becomes possible to determine the probabilities that the fetus will bear a certain inherited disease. This may allow the treatment of the disease shortly after birth using special diets or medicines or using genetic therapy, or, if treatment is not feasible, offers the option of terminating the pregnancy.

Such techniques have also become important in a number of other applications including in forensic medicine where typically only minute samples are available, in questions of paternity, and in the analysis of a sample for the presence of the DNA of a specific pathogen, for example, DNA of viral origin such as HIV.

As mentioned, many genetic diseases have multiple alternative genetic origins. Some of these diseases are fairly common in certain populations. For example: β-globin defective alleles, causing β-thalassemia, are widely spread in some Middle East populations; various defective CFTR alleles are carried in a heterozygous form by one of twenty individuals (5%) and the disease affects about $1/1600$ individuals of Caucasian descent in the world (Harrison's Principles of Internal Medicine 9th Ed. Isselbacher, Adams, Braunwald, Petersdorf and Wilson Eds. McGraw-Hill Book company, New York, pp. 1233). Because of the high frequency of Cystic Fibrosis and other genetically inherited disorders there is a widely recognized need for, and it would be highly advantageous to have, a low cost method, demanding merely non skilled personnel for it's execution, that enables the efficient and accurate detection of DNA sequence alterations in various genes of many individuals, simultaneously.

The most basic method for detection of point mutations is DNA sequencing, the most widely used sequencing method being based on the dideoxynueleotide chain termination procedure (See, Sanger F. (1981), Science 214, 1205–1210). The development of DNA and dideoxynucleotide conjugated fluorescent dyes, and suitable detection systems, enabled the improvement and the automatization of the basic dideoxy chain termination technique.

Other methods which have been used to determine the presence of alterations in known DNA sequences include ligase chain reaction (LCR); allele specific oligonucleotide (ASO) hybridization; reverse-ASO; restrictive site generating PCR (RG-PCR); denaturing/temperature gradient gel electrophoresis (D/TGGE); single strand conformation polymorphism (SSCP); heteroduplex analysis; restriction fragment length polymorphism (RFLP); PCR restriction fragment length polymorphism (PCR-RFLP); nuclease protection assays; chemical cleavage and other, less frequently used, methods.

These methods, although of great scientific importance, suffer from drawbacks limiting their routine use since they lack one or more of the following aspects rendering a method applicable for wide screening of various DNA alterations in many individuals. These aspects include: (1) Highly skilled personnel are needed for (a) accurate execution of the procedures, many of which include several complicated steps, specially gel electrophoresis and/or complicated blotting and hybridization procedures, and (b) for interpreting the results; (2) Strict calibration steps are needed before the examination of any new DNA alteration; (3) Theoretically some of the above mentioned procedures, are not suitable for the detection of all alterations; (4) Some are not applicable for the examination of DNA alterations in multiple sites simultaneously; (5) Some are time and effort consuming regarding the procedures themselves and/or the interpretation of their results; and last but definitely not least (6) Some of the procedures, specially those involving gel electrophoresis, are not easy to automate.

Recently, a novel method for the detection of point mutations which is based on a single nucleotide primer extension have been disclosed. See, Sokolov (1989) Nucleic Acids Research, 18(12), 3671; Kuppuswamy, M. H. et al. (1991) Proc. Natl. Acad. Sci. (U.S.A.) 88, 1143–1147; Singer-Sam, J., et al. (1992) in PCR Methods and Applications, Cold Spring Harbor Laboratory Press, Cold Spring Harbor, N.Y., U.S.A., pp. 160–163; and U.S. patent application Ser. No. 07/919,872, filed Jul. 27, 1992 which is incorporated by reference as if fully set forth herein. In this method, the DNA containing the putative mutation site is purified and than amplified by the use of PCR. The PCR fragments thus obtained are purified and denatured and several reaction mixtures are then prepared for each amplified fragment. Each reaction mixture contains a primer whose sequence is complementary to the genomic sequence 3' of and adjacent to the nucleotide base to be determined. The mixture further includes a radioactively or flourescently labeled nucleotide complementary to the normal coding sequence at the tested site or to a suspected mutant sequence at the site, and a DNA polymerase catalyzing the incorporation of the radioactively or flourescently labeled nucleotide into the primer, or equivalently, the extension of the primer by the radioactively or fluorescently labeled nucleotide. The primers are then separated from the template and the occurrence of radioactive or fluorescent labeling on the primers is determined. Aimed at increasing the radioactive or fluorescent signal, this procedure may be cycled provided that (i) the primer is in exes; (ii) the conditions applied for separating said primer from the template do not destroy or inhibit the DNA polymerase, alternatively, fresh DNA polymerase is added before each cycle. On this basis the subject may be identified as being normal (non-mutated, wild type), heterozygous or homozygous for the tested point mutation. This method, as well, requires an expert to follow its procedure particularly due to the need for high resolution polyacrylamide gel electrophoresis in analyzing the results.

A method circumventing the need for high resolution electrophoresis in analyzing the results, was presented in PCT/FI91/00046 (WO 91/13075). According to this method, the nucleic acid of interest is immobilized to a solid support. This is achieved via conjugating the nucleic acid of interest to an affinity group such as biotin which may be linked to avidin, streptavidin or antibiotin attached to the solid support. An oligonucleotide primer whose sequence is complementary to the genomic sequence adjacent to and 3' of the nucleotide base to be determined is annealed to the template DNA, a radioactively or flourescently labeled nucleotide complementary to the normal coding sequence at the tested site or to a suspected mutant sequence at the site, and a DNA polymerase catalyzing the incorporation of the nucleotide into the primer, or, equivalently, the extension of the primer by the labeled nucleotide. Washing off any non-incorporated nucleotides enables to determine the presence of extended primers in a gel electrophoresis independent manner, by determining the presence of radioactivity or fluorescence using fluorescent detector or radioactive counter, respectively, and thus the subject may be identified as being normal (non-mutated, wild type), heterozygous or homozygous for the tested point mutation. However, according to this procedure the reaction can not be cycled since the detection of primers which incorporated a labeled nucleotide is based upon such primers being annealed to the template DNA and therefore indirectly bound to the solid support during the washing stage. Separating the primers from the template DNA in order to enable the annealing of yet non-extended primer at the same location for further reaction cycles, will result in the loss of any former extended primer during the wash.

A more accurate and more advanced method which better addresses the detection of DNA alterations and foreign genetic material, circumventing the need for high resolution electrophoresis in analyzing the results, but at the same time enables cycling, was presented in U.S. patent application Ser. No. 08/084,505 filed 1 Jul., 1993 which is incorporated by reference as if fully set forth herein. According to this method, a primer, whose sequence is complementary to the genomic sequence adjacent to and 3' of the nucleotide base to be determined, is labeled (e.g., flourescently labeled) preferably at its 5'-end, and the extension moiety is a nucleotide or a nucleotide analog (e.g., dideoxynucleoside triphosphate) suitable for base pairing with the nucleotide positioned 5' to the last nucleotide base, paired with the primer's 3'-end nucleotide. Conjugated to the extension moiety is a separation moiety (e.g., biotin) enabling the affinity separation (e.g., via avidin, streptavidin or antibiotin attached to a solid support) of the extended primers from non-extended ones. DNA polymerase (e.g., Taq DNA polymerase) will enhance the rate at which the separation moiety conjugated extension nucleotide will be incorporated onto the labeled primer only if this nucleotide is complementary to the examined nucleotide base. Performing this reaction in four reaction vessels using in each the same primer but different extension nucleotide (e.g., deoxyribo or dideoxy (d/dd) ATP-, d/ddCTP-, d/ddGTP-, d/ddTTP-, d/ddUTP-biotin) and examining the fluorescence attached to, or eluted from, the solid support, obtained from each of the four reactions, enables the identification of the examined nucleotide base, and, furthermore, the genotype of the examined individual (i.e., normal, heterozygous or homozygous for the tested mutation). This method is simple to perform, does not require high resolution gel electrophoresis and may be cycled as many times as required to obtain high detection signals. Therefore, this method is more suitable for accurate and wide scale diagnostic purposes.

While this method presents an improvement in point mutation detection, a more practical method which better addresses the issue of simultaneous screening for more than one DNA alteration (or foreign genetic material) in more than one gene in more than one individual, is presented herein.

It is an object of the present invention to provide a simple, rapid and highly accurate method for detecting specific nucleotide sequences in various genes (or pathogens) of many individuals, simultaneously.

It is another object of the present invention to provide a diagnostic kit to be used for caring out the above method of the invention.

SUMMARY OF THE INVENTION

According to the present invention, there is provided a method, designated Specific Anchor Nucleotide Incorporation (SANI), for screening for the presence or absence of various specific DNA sequences and to enable complete genotyping, that is to determine the genotype (i.e., homozygote normal, heterozygote or homozygote mutant) of an individual or few individuals in many DNA loci of the same gene or different genes and combinations thereof, simultaneously.

The method of the invention depends on a novel tri-functional use of a primer extension unit, the primer extension unit including an extension moiety, a separation moiety and a detection moiety. The extension moiety of the primer extension unit is capable of specifically halting a nucleic acid template dependent primer extension in a manner which is strictly dependent on the identity of the unpaired nucleotide base on the template, immediately adjacent to, and 5' of the nucleotide base annealed with the 3'-end of the primer; the separation moiety permitting the affinity separation of primers thus extended by a primer extension unit from non-extended primers; and the detection moiety is enabling the detection of the primer extension unit incorporated onto extended primers.

The method of the invention also depends on the use of novel combinations of quatro-functioning oligonucleotides, each combination being suitable for the detection of the presence or of the absence of one type of nucleotide base (i.e., deoxyribo- or ribo-adenine, cytosine, guanine and thymine/uracil) in multiple target sequences optionally obtained, or derived by in vitro or in vivo amplification (e.g., polymerase chain reaction—PCR, or cloning, respectively), from one or many individuals. These functions include:

(1) Annealing function: Each oligonucleotide in each combination is complementary to a portion of the examined sequences adjacent to and 3' of one of the examined nucleotide bases. That is, each oligonucleotides is capable of annealing with a stretch of nucleotide bases present in the nucleic acid of interest immediately adjacent to the nucleotide base to be identified by it, so as to form a duplex between the oligonucleotide and the nucleic acid of interest such that the nucleotide base to be identified is the first unpaired base in the template immediately 5' of the nucleotide base annealed with the 3'-end of the oligonucleotide in the duplex.

(2) Priming function: The 3'-end of each oligonucleotide in each combination acts as a primer for a single nucleotide extension reaction. That is, each 3'-end of each primer directs the addition of a single primer extension unit, by a template dependent extension enzyme, provided that the nucleotide base to be identified is complementary to the primer extension unit, i.e., can form base pairing with the primer extension unit.

(3) Separation function: Conjugated to each oligonucleotide in each combination is a different affinity group (e.g., a hapten) enabling its separation from other oligonucleotides present in the combination by adsorption to affinity binding molecules (e.g., antibodies) adhered to a test surface. Preferably the unique sequence of each oligonucleotide in the combination is complementary to a matching oligonucleotide, adhered to a solid support, preferably a test surface, enabling the separation of each oligonucleotide by hybridization.

(4) Detection function: A detection moiety is conjugated to each oligonucleotide. The detection moiety conjugated to each oligonucleotide or to oligonucleotide groups may be of a different type. The oligonucleotide detection moiety is more suitable for the screening application of the method of the invention, and is used alternatively to the primer extension unit detection moiety, that is more suitable for the complete genotyping application.

One of the applications of the current invention is to enable quick screening of sequence alterations (e.g., point mutations) in many loci and individuals, simultaneously. This is achieved by pooling of several single nucleotide extension reactions into one reaction vessel. Pooling may be of few target sequences of the same individual, or of one target sequence of few individuals, or even, of few target sequences of few individuals. Such pooling are used for preliminary screening. A positive signal, preferably of the oligonucleotide detection moiety, from a pooled reaction would mean that: (a) when pooling few target sequences of the same individual, the tested subject carries at least one mutation in one of the examined sequences in a heterozygous or homozygous form; (b) when pooling one target sequence of few individuals, at least one of the individuals caries the examined mutation in a heterozygous or homozygous form; (c) when pooling few target sequences of few individuals, at least one of the individuals caries at least one of the examined mutations in a homozygous or heterozygous form. When few target sequences are examined simultaneously, each of the oligonucleotides or selected groups of oligonucleotides may be conjugated to a different type of a detection moiety. The method of the invention, therefore, makes it possible to test more samples at the same time as less reaction vessels are needed for any given number of examined sequences and individuals. This application of the present invention would minimize the cost of reagents per test and will also shorten the amount of time required to perform the tests. This application of the current invention is, therefore, very suitable for large scale screening of many individuals for many mutations, simultaneously. Furthermore, the results are final in cases where a negative signal is obtained, that is, no mutation is found in any of the examined sequences and/or individuals.

In the broad application of the method of the invention, four reactions are performed for each screen, a reaction for each of the four types of nucleotide bases (i.e., deoxyribo- or ribo-adenine, cytosine, guanine and thymine/uracil). In each reaction well, only the relevant oligonucleotide-template-primer extension unit combinations are present. That is, in each reaction (a) the templates, either from different loci of one or few genes, or from different individuals, or combinations thereof, are examined for the presence or absence of one type of nucleotide base (e.g., cytosine); (b) the oligonucleotides consisting the novel combination of oligonucleotides, are suitable for annealing with the examined DNA templates in a way that their 3'-ends (priming ends) are located 3' of and adjacent to the examined nucleotide bases; and (c) the extension moiety of the primer extension unit is suitable for base pairing with the examined nucleotide bases (e.g., GTP, dGTP or ddGTP). Assuming that one of the tested sequences, in one of the reaction mixtures (e.g., where the primer extension unit it dGTP), is harboring a mutation (e.g., cytosine instead of any other base) in a heterozygous or a homozygous form, some of the oligonucleotides in this mixture would become extended. Analysis of the reaction products, by affinity separation of extended oligonucleotides via the separation moiety of the primer extension unit, followed by a detection assay, preferably via the oligonucleotide detection moiety, will yield, in this case, a positive signal. On the other hand, if non of the tested sequences is harboring the mutation, that is, in the given example, the sequence may harbor any base but cytosine at the examined locations, analysis of the reaction products, preferably via the oligonucleotide detection moiety, will yield a negative signal. In the same manner other relevant oligonucleotide-template-primer extension unit combinations are pooled into reaction vessels definitively differing by the nature of the examined sequence alterations and the nature of the compatible extension moiety of the primer extension unit.

In a preferred use of this application of the present invention only two reaction vessels are used. In one of these reactions the extension moiety of the primer extension unit is an TTP/dTTP/UTP/dUTP, alternatively an TTP/dTTP/UTP/dUTP analog or an ATP/dATP, alternatively an ATP/dATP analog, and in the second reaction the extension moiety of the primer extension unit is a GTP/dGTP, alternatively GTP/dGTP analog or CTP/dCTP, alternatively CTP/dCTP analog. This is achieved by selecting oligonucleotides complementary to either one of the strands of tested DNA. For example if the examined nucleotide base in one of the examined sequences is a cytosine residue and in another sequence is a guanine residue, the relevant oligonucleotides are chosen in a way that each will anneal to the strand harboring the same nucleotide base, that is, to the coding strand of one of the examined sequences and to the non-coding strand, i.e., the complementary strand, of the other sequence.

Another application of the current invention enables complete genotyping of an individual, that is, to determine the genotype (i.e., homozygote-normal, heterozygote or homozygote-mutant) of an individual in many DNA loci, either of the same gene or different genes or combinations thereof. A further feature of this application, the simultaneous determination of the complete genotype, is achieved by performing two to four pooled single nucleotide extension reactions according to the broad, using four vessels, or preferably, the more economic screening application, using two vessels, of the method of the present invention, respectively. Then, via the oligonucleotide separation function, separating the different oligonucleotides by hybridization or affinity binding to complementary oligonucleotides or affinity molecules adhered to a solid support, preferably a test surface, respectively, and detecting, preferably via the detection moiety of the primer extension unit, those that have incorporated a primer extension unit. In this application it is possible that the detection will be partially contributed by the primer extension unit's detection moiety and partially by the 5'-end of the complementary oligonucleotide adhered to the test surface. Such detection is achieved by using marker conjugated antibodies raised against a hapten sharing properties of the detection moiety of the primer extension unit and a constant part of naturally included, or alternatively, conjugated to the 5'-end of the said oligonucleotide, rendering such detection-extension and hybridization dependent.

A third application of the current invention permits the use of only one type of primer extension unit's extension moiety conjugated to a separation and detection moieties to detect any specific sequence alteration. This is achieved by: (1) selecting primers capable of base pairing with stretches of DNA located 3' of but not necessarily adjacent to the nucleotide bases to be determined; and (2) using one to three primer extension units which are complementary to the nucleotide base in question and to nucleotide bases preceding or following it in direction of synthesis, of which only one primer extension unit is conjugated to a separation and detection moieties and may further include an extension terminating group (e.g., dideoxynucleotide-biotin), while the other primer extension units are not conjugated to a detection and separation moieties and are obligatorily containing a 3'-OH group. Different combinations of primer extension units devoid of the separation and detection moieties and one kind of primer extension unit conjugated to the separation and detection moieties is used for detection of different sequence alterations as described above. This results in a more uniform and efficient primer extension reaction and more uniform readings of positive and negative results.

All of the above applications of the presented method for detection of specific nucleotide bases depend upon obtaining a nucleotide triphosphate free aqueous solution of the examined genetic material. This is crucial especially when the genetic material is obtained by in vitro amplification (e.g., polymerase chain reaction, PCR) procedures that are dependent upon the presence of high concentration of triphosphate nucleotides during their execution. In the course of this research four strategies to avoid the interference of free nucleotides with the primer extension reaction were used. These include: (1) diluting the examined genetic material before contacting it with the primer extension reaction ingredients; (2) preferably including markedly high concentration of the primer extension unit; and/or (3) suitable combinations of triphosphate dideoxynucleotides, so as to compete with the triphosphate deoxyribonucleotides; or preferably, (4) the use of alkaline phosphatase to remove at least one phosphate group of the triphosphated nucleotides, rendering them inappropriate substrates for DNA polymerases, after which the alkaline phosphatase is inactivated by suitable means (e.g., heat). The simplicity of the latter approach renders it most suitable for diagnostic purposes.

According to features of preferred embodiments described below, the removal of the non-extended marked primers includes: (i) attaching the separation moiety of the primer extension unit to a solid support; and (ii) removing the marked primers not connected to the solid support.

According to further features of preferred embodiments of the invention described below, the separation moiety of the primer extension unit is capable of attaching to a solid support. An example of such a separation moiety is biotin which is capable of attaching to a solid support coated with avidin, streptavidin or antibiotin.

According to still further features in the described preferred embodiments, the extension moiety is a deoxyribonucleotide, such as dATP, dCTP, dGTP, dTTP and dUTP, a ribonucleotide such as ATP, CTP, GTP, TTP or a dideoxynucleotide, such as ddATP, ddCTP, ddGTP, ddTTP and ddUTP.

Also according to the present invention, there is provided a diagnostic kit for detecting the presence of specific nucleotide sequences in samples, consisting: (a) one or more primer extension units; (b) one or more combinations of marked oligonucleotide primers; (c) a template dependent extension enzyme; (d) at least one buffer; (e) a solid support for affinity separation of extended oligonucleotides via the separation moiety of the primer extension unit; and optionally (f) a solid support, preferably a test surface, for the separation of oligonucleotides via the oligonucleotide separation function.

A specific application of the method of the present invention is in the simultaneous identification of various point mutations at many loci of the same and of different genes and combinations thereof. The pooled oligonucleotides feature sequences which are complementary to the normal genes at a site 3' of, and immediately flanking, the putative mutation sites. The oligonucleotides preferably also feature a suitable marker.

Suitable extension moieties of primer extension units include those in which the hydroxyl group normally found attached to the 3' carbon is replaced with a different moiety such that once the primer extension unit is incorporated into an oligonucleotide primer, no other nucleotide may be bound to this modified nucleotide. Examples of such extension moieties include moieties wherein the 3'-OH groups has been replaced by -H, -SH and the like, including, but not limited to, various other substituent groups. Examples of extension moieties of primer extension units are deoxyribonucleotides, ribonucleotides, dideoxynucleotides or their analogs. The extension moiety may, for example, be attached to any suitable detection moiety, such as a radioactive label, e.g., $^{32}P$, and various fluorescent labels. Another example involves nucleotides having a biotin or similar moiety as an attachment which may function for indirect detection as well as for separation. The detection moiety of the primer extension unit may be a suitable hapten, which could be, for example, dinitrophenol (DNP), digoxigenin (DIG), sulfur species and the like, preferably biotin, which as mentioned may also facilitate the affinity separation of the extended primers.

The oligonucleotide primers may be of any suitable length. Time and expense considerations tend to shift preference toward shorter oligonucleotides which are still sufficiently long to ensure high sequence specificity while at the same time ensuring rapid, easy and accurate preparation. In the preferred embodiment all of the oligonucleotides share similar melting temperatures so as to render the optimum annealing and hybridization temperatures similar for all. The oligonucleotides can be substantially or precisely complementary to the complementary portion of the nucleic sequence being examined.

The sample of genetic material being tested by the above method may be in the form of RNA or DNA or a copolymer thereof extracted from biological samples or synthetically (e.g., chemically or enzymatically) prepared in vitro.

BRIEF DESCRIPTION OF THE DRAWINGS

The invention is herein described, by way of example only, with reference to the accompanying drawings, wherein:

FIGS. 5A–D present a schematic depiction of the operation of the preferred embodiment for the simultaneous detection for the existence or absence of a mutation in one or more of 5 different loci of the Gaucher gene of one patient, in two vessels.

DESCRIPTION OF THE PREFERRED EMBODIMENTS

The present invention is of a novel method for simultaneous identification of various nucleotide bases at specific positions in nucleic acids of interest.

The principles and operation of a method according to the present invention may be better understood with reference to the drawings and the accompanying description.

The present invention will be described in more detail with emphasis on a method for identifying point mutations in genes, which mutations are associated with genetic disorders. While this application of the method of the invention is presently preferred, this is by no means the only application of the invention as will no doubt be appreciated by those skilled in the art. For example, the method has various other applications including, but not limited to, the detection of specific genetic sequences in samples such as those associated with certain genetic diseases and pathogenic microorganisms, for example bacteria and viruses, in testing of paternity and in forensic medicine, cancers and plant and animal and human genetic polymorphism.

Figure 1:
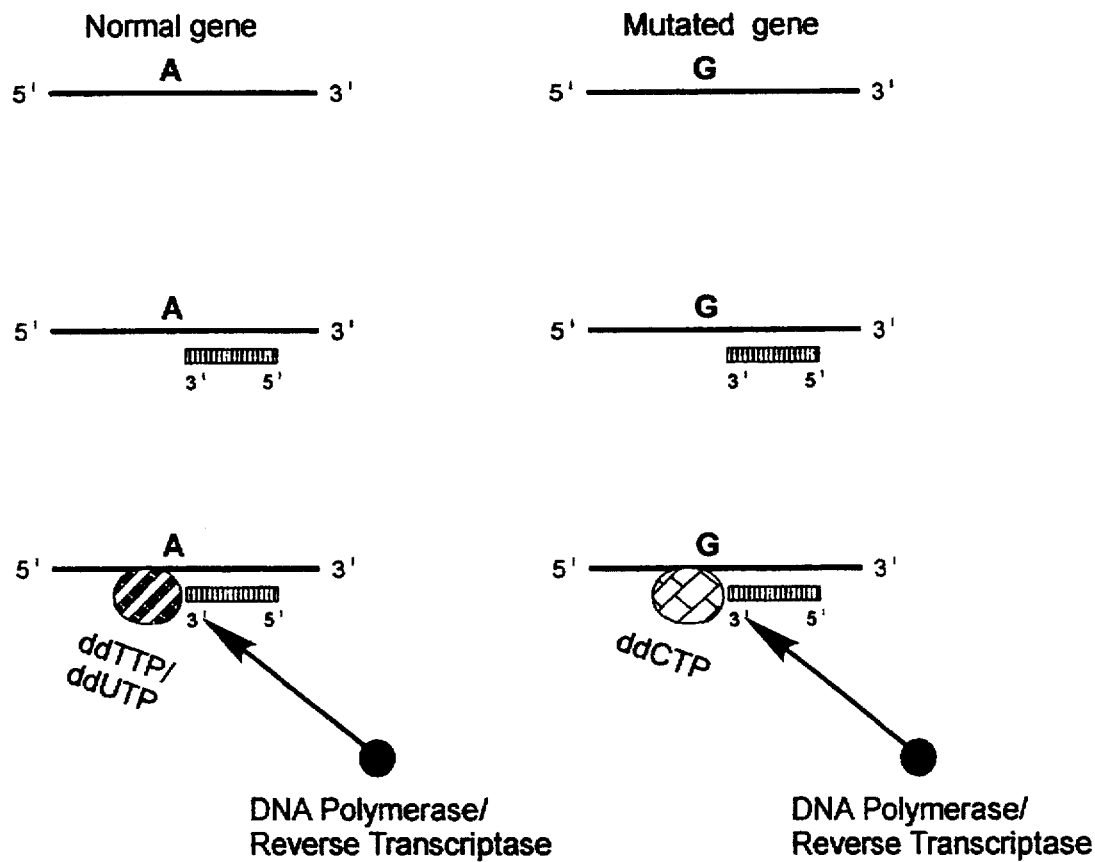
FIG. 1 is a schematic outline of features of a basic method for detecting point mutation in a known gene by means of nucleotide extension.
Figure 1A:
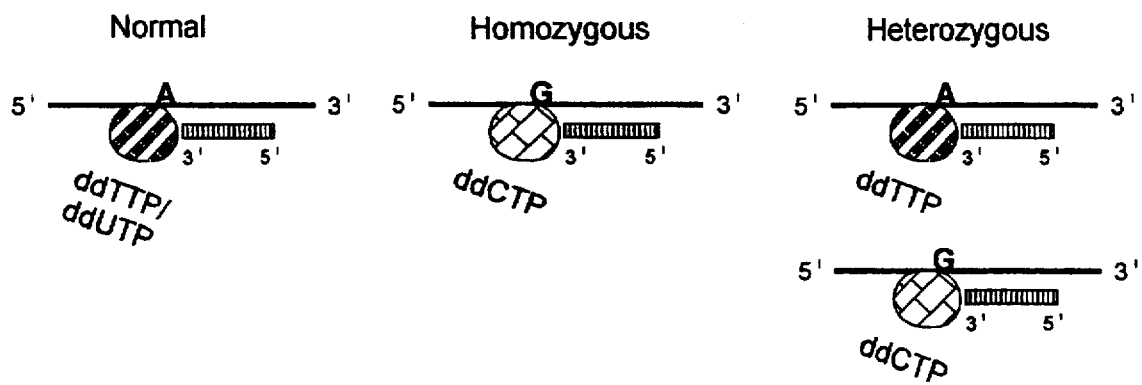

In order to better understand the preferred methods according to the present invention it is useful to first describe the basic method depicted schematically in FIG. 1. (A description of a related method is given in PCT/US92/01905 (WO 92/15712) and U.S. patent application Ser. No. 07/919, 872, filed Jul. 27, 1992 which is incorporated by reference as if fully set forth herein). To test for the occurrence of an A→G point mutation of a certain position in a known gene, a sample of DNA is obtained and a specific primer having a sequence which is complementary to the sequence of the region 3' of and immediately flanking the 3'-end of the suspected mutation site, is annealed to the sample. Labeled dideoxynucleotides (ddXTP) are then added together with a DNA polymerase. Following the incorporation reaction the primer is tested for incorporation of a terminator. In the case of a normal individual, only dideoxythymine (ddTTP) or dideoxyuracil (ddUTP) will be incorporated. On the other hand, if the individual is homozygous for the A→G mutation at that site only a dideoxycytosine (ddCTP) will be incorporated, whereas if the individual is heterozygous, i.e., one of its alleles is normal and the other is mutated, both dideoxythymine (or dideoxyuracil) and dideoxycytosine will be incorporated.

In its simplest form, the basic method for identifying point mutation may be summarized as follows:

(i) A sample of genetic material in the form to be analyzed is obtained in an aqueous carrier and annealed to a specific oligonucleotide primer having a sequence complementary to the template sequence 3' of, immediately flanking, the site of interest, e.g., the mutation site;

(ii) A set of one to four labeled chain elongation terminator nucleotides, for example, terminator nucleotide such as the dideoxynucleotides ddATP, ddCTP, ddGTP, ddTTP and ddUTP, or analogs thereof, are added to the mixture of (i);

(iii) A DNA polymerase is then added in an appropriate buffer, and an incorporation, or extension, reaction of the terminator nucleotides is thereby initiated;

(iv) After incorporation, or extension, a series of appropriate washes are carried out to remove the non-extended labeled terminator nucleotide, which removal can alternatively be accomplished using gel separation techniques; and (v) Labeling of the nucleotide primer is then determined by suitable analytical means, the labeling indicating the incorporation of a terminator nucleotide to the primer, and therefore provides an indication of the identity of the specific nucleotide base pair present at the mutation site.

Figure 2:
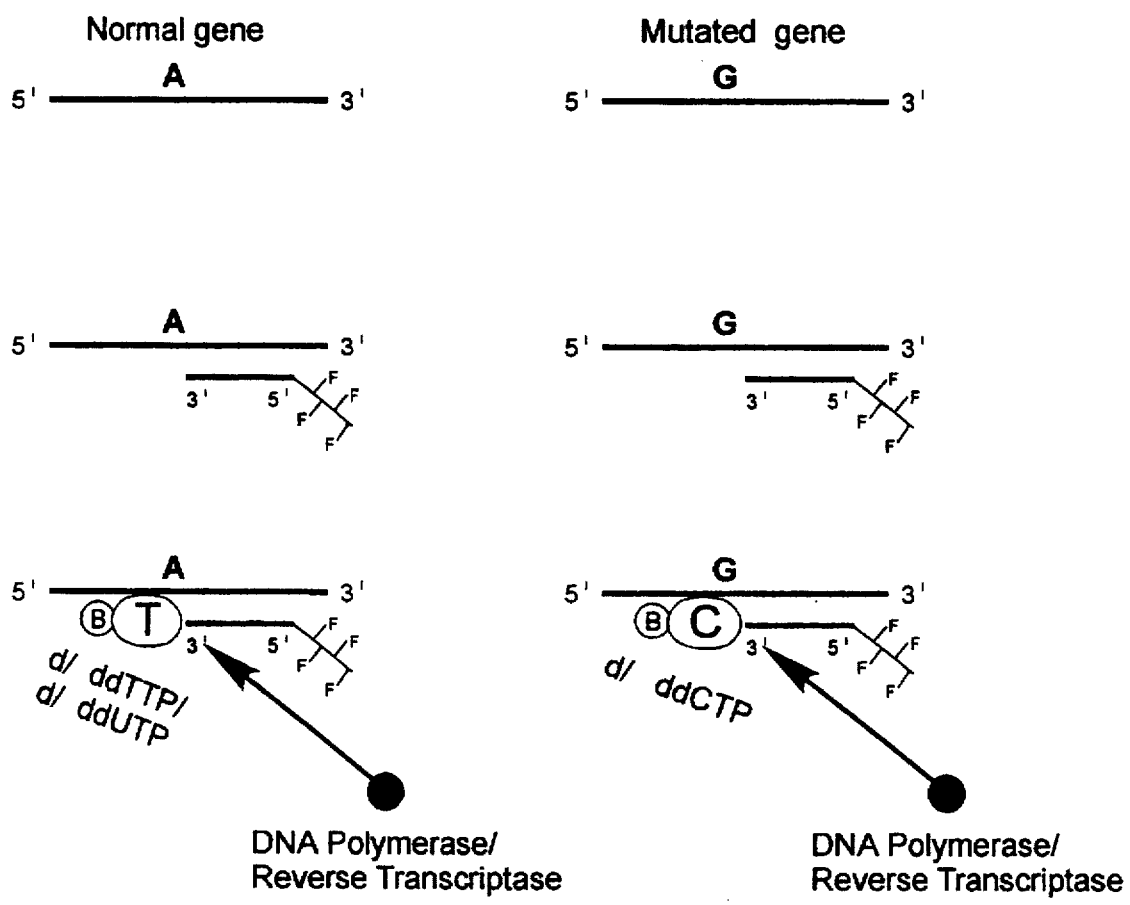
FIG. 2 is a schematic outline of features of the modified method for detecting point mutations in a known gene.
Figure 2A:
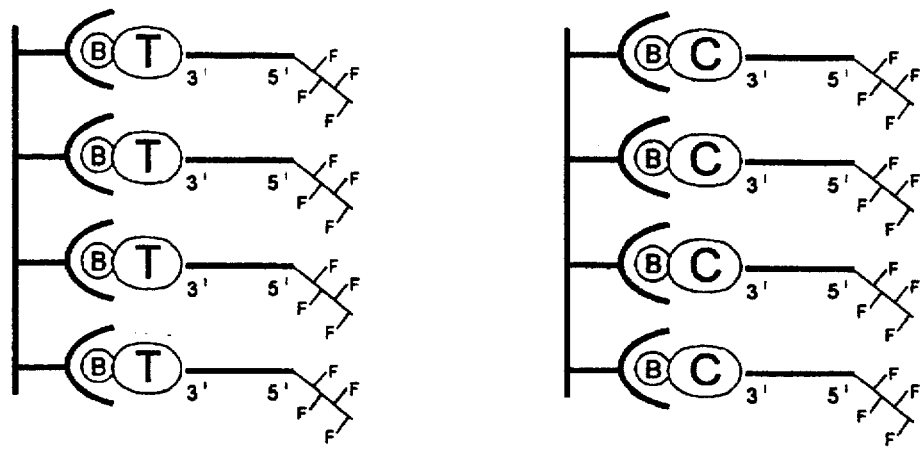

In order to even better understand the preferred methods according to the present invention it is useful to describe a modification of the above described basic method, depicted schematically in FIG. 2. A description of a related method is given in U.S. Ser. No. 08/084,505 which is incorporated by reference as if fully set forth herein. According to the modified method, the primer used is labeled with a suitable marker, fluorescent marker for example (denoted as 'F' in the Figure), while the primer extension unit includes a suitable separation moiety, such as a suitable hapten, which could be, for example, dinitrophenol (DNP), digoxigenin (DIG), sulfur species and the like, preferably, biotin (denoted as 'B' in the Figure), which facilitates the affinity separation of the extended primer. More specifically, the identity of a nucleotide base at a specific position in a nucleic acid of interest can be determined by carrying out a process, somewhat similar to that described above but using a marked primer and a biotinylated primer extension unit.

Thus, if the nucleic acid is double stranded, a sample containing the nucleic acid of interest is first treated to obtain unpaired nucleotide bases spanning the specific position to be analyzed. If the nucleic acid of interest is single stranded, this step can be skipped.

The unpaired nucleotide bases spanning the specific position are then contacted, under hybridizing conditions, with the marked oligonucleotide primer which is capable of annealing with a stretch of nucleotide bases present in the nucleic acid of interest adjacent to, and 3' of, the nucleotide base to be identified. The result is the formation of a duplex between the primer and the nucleic acid of interest such that the nucleotide base to be identified is the first unpaired base in the template immediately 5' of the nucleotide base annealed with the 3'-end of the primer in the duplex.

A special reagent useful in determining the identity of a nucleotide base at a specific position in a nucleic acid of interest includes an aqueous carrier and one or more primer extension units. The primer extension unit includes an extension moiety and a separation moiety described above which are linked together. The extension moiety is capable of specifically halting a nucleic acid template dependent, primer extension reaction in a manner which is strictly dependent on the identity of the unpaired nucleotide base of the template immediately adjacent to, and 3' of, the 3'-end of the primer. The separation moiety permits the affinity separation of the primer extension unit from unincorporated reagent and nucleic acid.

The duplex formed above is contacted with a special reagent, such as that described above, under conditions permitting the base pairing of the complementary extension moiety of the primer extension unit present in the reagent with the nucleotide base to be identified and the occurrence of a template dependent, primer extension reaction to incorporate the extension moiety of the primer extension unit at the 3'-end of the primer, resulting in the extension of the primer usually by a single unit.

Once the extension of the marked primer by the primer extension unit has been effected, any non-extended marked primers are removed by any suitable technique and any suitable technique is used to determine the identity of the extended primers.

In a preferred embodiment of the method of the present invention, employed is a novel tri-functional use primer extension unit, the primer extension unit including an extension moiety, a separation moiety and a detection moiety. The extension moiety of the primer extension unit is capable of specifically halting a nucleic acid template dependent primer extension in a manner which is strictly dependent on the identity of the unpaired nucleotide base on the template, immediately adjacent to, and 5' of the nucleotide base annealed with the 3'-end of the primer; the separation moiety permitting the affinity separation of primers extended by a primer extension unit from non extended primers, different types of extension units may be conjugated to different types of separation moieties; and the detection moiety enabling the detection of the primer extension unit of extended primers.

In the preferred embodiment of the method of the present invention, employed are, also, novel combinations of quatro-functioning oligonucleotides, each combination being suitable for the detection of the presence or of the absence of one type of nucleotide base (i.e., deoxyribo- or ribo-adenine, cytosine, guanine and thymine/uracil) in multiple target sequences optionally obtained, or derived by in vitro amplification (e.g., polymerase chain reaction, PCR), from one or many individuals. These functions include annealing, priming, separation and detection functions. For the annealing function each oligonucleotide in each combination is made complementary to a portion of one of the examined sequences adjacent to and 3' of one of the examined nucleotide bases. That is, each of the oligonucleotides is capable of annealing with a stretch of nucleotide bases present in the nucleic acid of interest immediately adjacent to the nucleotide base to be identified by it, so as to form a duplex between the oligonucleotide and the nucleic acid of interest such that the nucleotide base to be identified is the first unpaired base in the template immediately 5' of the nucleotide base annealed with the 3'-end of the oligonucleotide in the duplex. For the priming function the 3'-end of each oligonucleotide in each combination is made as to enable it to act as a primer for a single nucleotide extension reaction. That is, each 3'-end in each combination directs the addition of a single primer extension unit, by template dependent extension enzyme, provided that the nucleotide base to be identified is complementary to the primer extension unit, i.e., can form base pairing with the primer extension unit extension moiety. For the separation function each oligonucleotide in each combination is either complementary to a matching oligonucleotide, adhered to a solid support, preferably a test surface, enabling the separation of each oligonucleotide by hybridization or conjugated to an affinity molecule enabling it's separation by affinity binding to complementary affinity molecules adhered to the solid support, preferably a test surface. For the detection function, to each of the oligonucleotides, conjugated is a detection moiety. The detection moiety conjugated to each of the oligonucleotides may be of a different type. The oligonucleotides detection moiety is more suitable for the screening application of the method of the invention, and is used alternatively to the primer extension unit detection moiety, that is more suitable for the complete genotyping application.

More specifically, under this preferred embodiment, an efficient and quick screening of sequence alterations (e.g., point mutations) is achieved by carrying out a process, somewhat similar to that described above using marked primers and a biotinylated primer extension unit via pooling of several single nucleotide extension reactions into one reaction vessel. Pooling may be of few target sequences of the same individual, or of one target sequence of few individuals, or even, of few target sequences of few individuals. Such pooling are used for preliminary screening of many nucleotide bases at specific positions. Thus, if the nucleic acids are double stranded, a sample containing the nucleic acids of interest is first treated to obtain unpaired nucleotide bases spanning the specific positions. If the nucleic acids of interest are single stranded, this step can be skipped.

The unpaired nucleotide bases spanning the positions are then contacted, under annealing conditions, with combinations of marked oligonucleotide primers which are capable of annealing with stretches of nucleotide bases present in the nucleic acids of interest adjacent to, and 3' of, each of the nucleotide bases to be identified. The result is the formation of duplexes between the primers and the nucleic acids of interest such that the nucleotide bases to be identified are, in each case, the first unpaired base in the template immediately 5' of the nucleotide base annealed with the 3'-end of the primer in each duplex.

A special reagent useful in determining the identity of nucleotide bases at specific positions in nucleic acids of interest includes an aqueous carrier and one or more primer extension units. The primer extension unit includes an extension moiety, a separation moiety and a detection moiety, described above, which are linked together. The extension moiety is capable of specifically halting a nucleic acid template dependent, primer extension reaction in a manner which is strictly dependent on the identity of the unpaired nucleotide base of the template immediately adjacent to, and 3' of, the 3'-end of the primer. The separation moiety permits the affinity separation of the primer extension unit incorporated onto oligonucleotide primers from unextended oligonucleotides and nucleic acid. The detection moiety permits the detection and identification of thus extended oligonucleotides.

The duplex formed above is contacted with a special reagent, such as that described above, under conditions permitting the base pairing of the complementary extension moiety of the primer extension unit present in the reagent with the nucleotide bases to be identified and the occurrence of a template dependent, primer extension reactions to incorporate extension moieties of the primer extension unit at the 3'-end of the various oligonucleotide primers in the combination, resulting in the extension of each of the primers by a single unit.

In the broad application of this embodiment of the invention, four reactions are performed for each screen, a reaction for each of the four bases (i.e., deoxyribo- or ribo-adenine, cytosine, guanine and thymine/uracil). In each reaction vessel, only the relevant oligonucleotides-templates-primer extension unit combinations are present. That is, in each reaction (a) the templates are examined for the presence of one type of nucleotide base; (b) the oligonucleotides consisting the novel combination of oligonucleotides, are suitable for annealing with the examined DNA templates in a way that their 3'-ends (priming ends) are located 3' of and adjacent to the examined nucleotide bases; and (c) the extension moiety of the primer extension unit is suitable for base pairing with the examined type of nucleotide bases.

In a preferred and more economic application of this embodiment of the present invention only two reactions are performed. In one of these reactions the extension moiety of the primer extension unit is an dTTP or preferably an dATP, or their ribonucleotides or other analogs, and in the second reaction the extension moiety of the primer extension unit is an dCTP or preferably an dGTP or their ribonucleotide or other analogs. This is achieved by selecting oligonucleotides complementary to either one of the strands of the tested DNA.

Once the extension of the marked primers by the primer extension unit has been effected, any non-extended marked primers are removed by any suitable technique and any suitable technique is used to determine the presence of thus extended primers.

After performing two or four pooled single nucleotide extension reactions according to the broad or the preferred screening application of the embodiment of the present invention, respectively, provided that the presence of extended primers was detected, the identity of thus extended primers is determined simultaneously via their assortment, which assortment is achieved by the separating function of the oligonucleotides preferably via hybridization to complementary oligonucleotides adhered to a solid support, preferably a test surface, and detecting, preferably via the detection moiety of the primer extension unit, those that have incorporated a primer extension unit.

For some applications different types of primer extension units may be conjugated to different types of separation moieties. This enables: (1) when using one marked primer, to determine the nucleotide sequence and the genotype of an examined individual at a specific locus by affinity separation of extended primers using complementary affinity molecules adhered at different locations to a test surface, each capable of binding one type of primer extension unit followed by detection of thus adhered extended primers via the detection moiety of the primer extension unit or preferably the oligonucleotide primer detection function; and (2) when using a combination of marked primers, each oligonucleotide primer is conjugated to a different detection group, to determine the nucleotide sequence and the complete genotype of an examined individual at few loci by affinity separation of extended primers using complementary affinity molecules adhered at different locations to a test surface, each capable of binding one type of primer extension unit followed by detection of thus adhered extended primers via the detection moiety of the oligonucleotide primer.

According to the embodiment of the present invention, the primers consisting the novel oligonucleotide combinations may be marked with any suitable marker, including, but not limited to species which provide fluorescence, chemiluminescence, or radioactivity, as well as species such as catalysts, enzymes, substrates and coenzymes. Furthermore, each oligonucleotide or groups of oligonucleotides of any oligonucleotide combination may be marked with a different type of marker, that is any oligonucleotide may be conjugated to a different type of a detection moiety.

Preferably, the separation moiety of the primer extension unit, is capable of attaching to a solid support. Preferably, the separation moiety of the primer extension unit includes biotin which permits affinity separation of the primer attached to the extension moiety of the primer extension unit from non-extended primers and from the nucleic acids of interest through the binding of the biotin to streptavidin, avidin or antibiotin attached to a solid support.

Preferably, but by no means essentially, the separation moiety of the primer extension unit functions as a detection moiety as well. Shared separation/detection moieties could include a suitable hapten, which could be, for example, dinitrophenol (DNP), digoxigenin (DIG), sulfur species and the like, preferably, biotin, which facilitates the affinity separation of the extended primers as well as the indirect detection of the extended primers via an affinity detection assay.

Any suitable extension moiety of the primer extension unit may be used. Preferably, the extension moiety is deoxyribonucleotide, such as dATP, dCTP, dGTP, dTTP and dUTP, most preferably a dideoxynucleotide, such as ddATP, ddCTP, ddGTP, ddTTP and ddUTP.

The removal of the non-extended marked primers may be accomplished in various ways. Before the removal can be effected it is normally necessary to separate the primer from the nucleic acid of interest. This is typically accomplished by use of appropriate denaturing conditions. Preferably, the removal of the non-extended marked primer is effected by first attaching the separation moiety of the primer extension unit to a solid support and then removing, as by washing, any marked primer not connected to the solid support.

The identity of the extended primers can be determined in any suitable way, depending on the mature of the marker used to mark the primers, the detection moiety of the primer extension unit and other factors. Preferably, the determination of the identity of the extended marked primers is carried out following their attachment to a solid support via the separation moiety of the primer extension trait. Thus, if the primer extension unit was able to extend the primers, the marked primers will be detected as being attached to the solid support. In this case the extended primers will be eluted from the solid support, by means depending on the nature of the separation moiety of the primer extension unit, and will be sorted preferably via the oligonucleotide separation function by hybridization to complementary oligonucleotides adhered to a second solid support, preferably a test surface. The presence of extended primers bound to the test surface may be detected via the detecting function of the marked primers, or alternatively, and preferably, by the detection moiety of the primer extension unit. On the other hand, if the primer extension unit was not able to extend the primer, only the primer extension units, but no primers, will be attached to the solid support, leading to the failure to detect the marked primers and, therefore, to the end of the detection procedure.

It is preferred but by no means essential to separate the extended primers from non-extended ones prior to their identification by assortment via the oligonucleotide separating function as delineated above. In this case the detection of extended and assorted primers is based solitary upon the detection moiety of the primer extension unit.

In a further embodiment of the method of the present invention only one kind of primer extension unit's extension moiety, conjugated to a separation and detection moieties, is used for the detection of a specific sequence alteration. A third application of the current invention permits the use of only one type of primer extension unit's extension moiety conjugated to a separation and detection moieties to detect any specific sequence alteration. This is achieved by selecting primers capable of base pairing with stretches of DNA located 3' of but not necessarily adjacent to the nucleotide bases to be determined; and using one to three primer extension units which are complementary to the nucleotide base in question and to nucleotide bases preceding or following it in direction of synthesis, of which only one primer extension unit is conjugated to a separation and detection moieties and may further include an extension terminating group (e.g., dideoxynucleotide-biotin), while the other primer extension units are not conjugated to a detection and separation moieties and are obligatorily containing a 3'-OH group. Different combinations of primer extension units devoid of the separation and detection moieties and one kind of primer extension unit conjugated to the separation and detection moieties is used for detection of different sequence alterations as described above. This results in a more uniform and efficient primer extension reaction and more uniform readings of positive and negative results. For example consider the point mutation T→G. Assume that the examined nucleotide base is followed by an A nucleotide base in direction of synthesis. One would use two reaction vessels, each containing the examined DNA template; a primer extension unit conjugated to a separation and detection moiety capable of base pairing with the nucleotide base following the examined nucleotide base (e.g., d/ddTTP or d/ddUTP); an oligonucleotide primer having a sequence which is complementary to the sequence of the region 3' of and immediately flanking the 3'-end of the suspected mutation site; and a suitable salts buffer. In addition, one of the reaction mixtures contains a primer extension unit capable of base pairing with the normal sequence (e.g., dATP), while the other contains a primer extension unit capable of base pairing with the examined nucleotide base in the mutated sequence (e.g., dCTP). Contacting the mixtures with a template dependent DNA polymerase results in extension of the oligonucleotide primer by two primer extension units in the first or the second reaction, provided that the examined individual is homozygote for either the normal or the mutated sequence, respectively. On the other hand, if the examined individual is heterozygote, the primers in both reactions, will be extended by two primer extension units. Once the extension of the marked primer by the primer extension units has been effected, any non-extended marked primers are removed by any suitable technique and any suitable technique is used to determine the identity of the extended primer.

Methods according to preferred embodiments of the present invention enjoy a number of advantages relative to the basic method and the modified method described above.

As far as the basic method is concerned:

First, the marking of the primer can be done in such a way as to incorporate a large and unmistakable marker, e.g., a relatively long chain of fluorescent moieties, which can be easily picked up by simple fluorometers. It is estimated that the marked primer may be up to 30 times easier to detect than the marked terminators used in the basic method.

Second, the marked primers used in the preferred embodiments are much easier to produce than the marked fluorescent terminators of the basic method.

Third, marked fluorescent terminators are highly polymerase dependent. See, for example, Lee, L. G. et al., Nucleic Acids Research, 1992, 20(10) 2471–2483, 2472, which states that a disadvantage of dye-labeled terminators is that they must be tailored to a specific DNA polymerase.

Fourth, in cases where primer dependent in vitro amplification products are used as genetic material for template dependent primer extension, residual amplification primers may be extended, resulting in false positive signal if the primer extension unit is labeled but not if the primer used for the extension reaction is labeled.

Fifth, fluorescently marked primers used in the preferred embodiments are more stable than the corresponding marked terminators of the basic method. An added complication with the marked terminators of the basic method is that the different terminators which are marked in the same way display different degrees of stability. See, for example, Ansorge W., et al., (1993) Methods Mol. Biol. U.S.A. 23:317–356. These complications significantly limit the applicability of the basic method in commercial tests.

Finally, the need for high resolution gel electrophoresis is eliminated.

As far as the gel electrophoresis independent method, described under PCT/FI91/00046 (WO 91/13075) is concerned:

The method of the present invention makes it possible to cycle the reaction as many times as needed for unequivocal determination of the presence or absence of a signal from the marked oligonucleotide primers, reflecting the extension of said primers by a primer extension unit.

As far as the modified method is concerned:

The method of the present invention makes it possible to test more samples at the same time as less reaction vessels are needed per any given number of examined sequences and individuals. This application of the present invention would (i) minimize the cost of reagents per test and (ii) will also shorten the amount of time required to perform the tests. This application of the current invention is, therefore, very suitable for wide screening of many individuals for many mutations, simultaneously. Furthermore, the results of the screening application of the preferred embodiment are the final results in cases where a negative signal is obtained, that is, no mutation is found in any of the examined sequences and individuals. Since different DNA polymerases incorporate different nucleotide derivatives at differing efficiencies, by letting the differentiating nucleotide be a non-labeled dXTP (dATP and dCTP in the above given example) and using the same labeling nucleotide whether the template is normal or mutant, obtained is a much stronger label— sometimes an order of magnitude stronger and a more uniform labeling of the normal or mutant templates of heterozygotes as well as the elimination of the need for tedious calibrations during the routine execution of the examinations.

The genetic material to be analyzed may, in principle, be any RNA or DNA obtained from the tissues or body fluids of humans, animals or plants or obtained from cultures of microorganisms or human, animal or plant cells or nucleic acid synthesized by polymerase. The genetic material may alternatively be obtained from non-living sources suspected of containing matter from living organism sources, as may be the case when applying the method in forensic medicine for detecting and identifying specific nucleotide sequences present in or on samples of clothing, furniture, weapons and other items found at the scene of a crime. In this instance, the of DNA, since any obtained is usually in the form of DNA, since any RNA in such samples would normally have been degraded by ribonucleases.

The specific application of the inventive method for the detection and identification of mutations and/or polymorphism in genes having a known sequence is presently a preferred embodiment. In this application the method may be used as a diagnostic assay to determine specific mutations present in individuals suffering from, or showing symptoms of, diseases known to be caused by one or more point mutations in specific genes. The method may also be applied for simultaneous screening of healthy individuals to determine whether they are carriers, i.e., heterozygous for mutations linked to known diseases or predispositions. This is the case, for example, in the well elucidated Tay-Sachs disease in which diseased individuals have mutations in both alleles encoding the hexoaminidase A gene, and carriers of the disease have one or more mutations in one allele only. Furthermore, the method may also be applied for screening embryos by analyzing samples of amniotic fluid cells to simultaneously determine whether the embryos have any known mutations in one or two or none of the alleles of a gene or genes known to be associated with specific genetic diseases.

The sample of nucleic acids can be drawn from any source and may be natural or synthetic. The sample of nucleic acids may be made up of deoxyribonucleic acids, ribonucleic acids, or copolymers of deoxyribonucleic acid and ribonucleic acid or combinations thereof. The nucleic acid of interest can be synthesized enzymatically in vitro, or synthesized non-enzymatically. The sample containing the nucleic acid or acids of interest can also comprise extragenomic DNA from an organism, RNA transcripts thereof, or cDNA prepared from RNA transcripts thereof. Also, the nucleic acid or acids of interest can be synthesized by the polymerase chain reaction.

The oligonucleotide primers may be any suitable species, preferably an oligodeoxyribonucleotide, an oligoribonucleotide, a protein nucleic acid or a copolymer of deoxyribonucleotides, ribonucleotides and protein nucleic acids. The oligonucleotide primers can be either natural or synthetic. The oligonucleotide primers can be synthesized enzymatically in vivo, enzymatically in vitro, or non-enzymatically in vitro. The oligonucleotide primers can be labeled with a detectable marker, which marker may be different for each oligonucleotide or groups of oligonucleotides. The marker can be different from any other detectable marker present in the reagent or attached to the nucleic acid of interest. In addition, the oligonucleotide primers must be capable of hybridizing or annealing with stretches of nucleotide bases present in the nucleic acids of interest, immediately adjacent to, and 3' of, the nucleotide bases to be identified. One way to accomplish the desired hybridization is to have the template dependent primers be substantially complementary or fully complementary to the known base sequences immediately adjacent the bases to be identified.

The oligonucleotide primers can be any length or sequence, can be DNA or RNA, or any modification thereof. It is necessary, however, that the length of the primers be chosen to optimize the specificity of the hybridization to the target sequences of interest.

The primers can be separated from the nucleic acid of interest after the extension reaction by using appropriate denaturing conditions, which may include heat, alkali, formamide, urea, glyoxal, enzymes, and combinations thereof.

Different versions of the method for determining the identity of a nucleotide base at a specific position in a nucleic acid of interest and the method for determining the presence or absence of particular nucleotide sequences in a sample of nucleic acids are possible. In one version, the template is deoxyribonucleic acid, each primer is an oligodeoxyribonucleotide, oligoribonucleotide, or a copolymer of deoxyribonucleotides and ribonucleotides, and the template dependent enzyme is a DNA polymerase.

In a second version, the template is a ribonucleic acid, each primer is an oligodeoxyribonucleotide, oligoribonucleotide, or a copolymer of deoxyribonucleotides and ribonucleotides, and the template dependent enzyme is a reverse transcriptase.

In a third version, the template is a deoxyribonucleic acid, each primer is an oligoribonucleotide, and the enzyme is an RNA polymerase.

In a fourth version, the template is a ribonucleic acid, each primer is an oligoribonucleotide, and the template dependent enzyme is an RNA replicase.

The nucleic acid of interest may contain non-natural nucleotide analogs such as deoxyinoside or 7-deaza-2'-deoxyguanosine. These analogs destabilize DNA duplexes and could allow a primer annealing and extension reaction to occur in a double stranded sample without completely separating the strands.

A method according to the present invention can be used to determine the identity of nucleotide bases at different alleles each of a specific position in nucleic acids of interest via the procedure as described above using at least two separate vessels. The reagent used in each vessel contains a primer extension unit having a different extension moiety.

A method according to the present invention can also be used to type a sample containing nucleic acids. Such a process includes identifying the nucleotide base or bases at each of one or more specific positions, each such nucleotide base being identified simultaneously using a different primer in an oligonucleotide combination by the method as described above.

A method according to the present invention can be further used to identify different alleles in a sample containing nucleic acids. Such a process includes identifying the nucleotide base or bases present at each of one or more specific positions, each of such nucleotide bases being identified by the method described above.

Another application of a method according to the present invention is in the determination of the genotype of an organism at one or more particular genetic loci. Such a process calls for obtaining from the organism a sample containing genomic, mitochondrial or chloroplast DNA. The nucleotide base or bases present at each of one or more specific positions in nucleic acids of interest is identified by the process described above. In this way, different alleles are identified and, in turn, the genotype of the organism is determined at one or more particular genetic loci.

The subject invention also provides a method of typing a sample of nucleic acids which consists of identifying the base or bases present at each of one or more specific positions, all such nucleotide bases being identified simultaneously using one of the methods for determining the identity of nucleotide bases at a specific positions in nucleic acids of interest as outlined above. Each specific position in the nucleic acids of interest is determined using a different primer in a primer combination. The identity of each nucleotide base or bases at each position can be determined individually or, preferably, the identities of the nucleotide bases at different positions can be determined simultaneously.

The subject invention also provides another method of typing a sample of nucleic acids which comprises determining the presence of absence of one or more particular nucleotides sequences, the presence of absence of each such nucleotide sequence being determined using one of the methods for determining the presence or absence of a particular nucleotide sequence in a sample of nucleic acids as outlined above.

The subject invention also provides an additional method of typing a sample containing nucleic acids. First, the presence or absence of one or more particular nucleotide sequences is determined, simultaneously; the presence or absence of each such nucleotide sequence is determined using one of the methods for determining the presence or absence of a particular nucleotide sequence in a sample of nucleic acids as outline above. Second, the nucleotide base or bases present at each of one or more specific positions is identified; each such base is identified using one of the methods for determining the identity of a nucleotide base at a specific position in a nucleic acid of interest as outlined above.

The subject invention further provides a method for identifying different alleles in a sample containing nucleic acids which comprises identifying the base or bases present at each of one or more specific positions. The identity of each nucleotide base is determined by the method for determining the identity of a nucleotide base at a specific position in a nucleic acid of interest as outlined above.

One or more primer extension units as described above, in combination with one or more appropriate marked oligonucleotide primer combinations, and a DNA polymerase, and an appropriate salt and cofactor mixture, can be used under appropriate hybridization conditions as a kit for diagnosing or typing nucleic acids. The kit further includes an appropriate solid support, test surface and suitable buffers, such as binding solutions wash solutions and surface hybridization solutions.

The conditions for the occurrence of the template dependent, primer extension reaction can be created, in part, by the presence of a suitable template dependent enzyme. Some of the suitable template dependent enzymes are DNA polymerases.

Table I lists a sampling of the various diseases which are known to result from the presence of one or more mutations in a gene encoding a specific protein or enzyme. Most of these diseases are recessive diseases, i.e., the diseased individual has both alleles carrying a mutation, the mutation resulting in the protein being absent (gene not expressed); being in an inactive state (having an altered amino acid sequence); or being present in less than the required amounts (significantly reduced gene expression).

TABLE I

| DISEASE | GENE |
| --- | --- |
| Hemophilia A | factor VIII |
| Hemophilia B | factor IX |
| Lesch-Nyhan syndrome | HPRT |
| Ornithine transcarbamylase | OTC |
| Hereditary Amyloidosis (HA) | transthyretin (TTR) |
| Gaucher | glucocerebrosidase |
| Cystic Fibrosis | CFTR |
| Osteogenesis imperfecta | collagen (I, II), procollagen |
| Hemoglobinopathies (e.g., β-thalassemia, Sickle cell anemia) | hemoglobin genes |
| Acute intermittent porphyria (AIP) | uroporphyrinogen I synthetase |
| Phenylketonuria | phenylalanine hydroxylase |
| Tay Sachs | hexosaminidase A (HEXA) |
| Familial hypercholesterolemia (FH) | LDL receptor |
| Neurofibromatosis | NF1 |

The ongoing research to determine the genetic basis for diseases and the advent of technologies such as the polymerase chain reaction (PCR) has resulted in the discovery and complete sequencing of more and more genes encoding structural protein or enzyme products, a mutation in which would lead to either no expression of the gene product or expression of a product which is qualitatively or quantitatively impaired and thereby resulting in a disease. There is thus an ever expanding field of application of the above method of the invention.

The method of the invention, besides having use in diagnosis of specific disease linked mutations in known gene regions, may also be of use in testing for the presence of a specific sequences associate with blood typing, tissue classification—HLA-typing, sex determination or possible susceptibility of an individual to certain diseases. Tissue classifications, for example, may be determined by identifying polymorphism being specific for a particular individual. Screening these known HLA gene sequences by the present method may also be used as a diagnostic tool to determine whether the individuals in question are susceptible to certain diseases, e.g., various specific autoimmune diseases which are correlated with the specific HLA genes carried by the individual.

As noted above, the method of the invention may also be applied in the field of forensic medicine in which polymorphism in specific genes, e.g., the β-globin gene cluster and the various known repeat sequences, can be determined in, for example, blood or semen samples obtained at the scene of a crime and the results used to indicate whether or not a particular suspect was involved in the crime. Similarly, the aforesaid determination may also be used to determine whether a certain male individual is the father in cases of disputed paternity.

There is evidence that certain cancers may be the result of specific point mutation in the sequence of certain genes and, accordingly, the present methods may be used as an early diagnostic tool to screen the general population or those individuals considered most likely to develop such cancers.

Another application of the present methods, as noted above, is the detection of microorganisms in a sample on the basis of the presence of specific sequences in the sample. For example, an individual suspected of being infected by a microorganism, such as a bacteria or virus, can be tested by using a combination of oligonucleotide which anneal only with a specific bacterial and/or viral DNA sequences and not with sequences present in the individual. One example of such an application is in the screening of individuals for the presence of the AIDS virus. Moreover, by application of the present method the specific strain of virus, e.g., HIS-I, HIV-II, or HIV-III, may also be determined in a sample or few samples simultaneously. Similarly, different species or strains of bacteria in a sample may be distinguished one from the other, e.g., the presence of Shigella vs. Salmonella bacteria which are difficult to distinguish from one another by standard techniques.

Gene regions corresponding to all of those set forth in Table I above and many others, may be analyzed for the presence of one or more point mutations at any number of sites within the gene region, or the existence of polymorphism for any specific allele, or whether the individual being tested is homozygous for a specific base pair mutation, heterozygous therefor (i.e. carrier) or whether the individual is normal for this specific base pair (i.e. carrying two normal alleles).

The present method can be a very effective alternative for the traditional mutation detection methods which use radioactive material, different hybridization or PCR conditions for every mutation, specific gels or an expensive automated sequencer. The present method enables a large scale diagnostic procedure for multi-mutation detection with the possibility of screening many different samples, simultaneously, in a short period of time. Furthermore, the present method provides a means for population screening of the multi-mutations in a wide range of inherited diseases and genetic disorders such as genetic cancers and the like, and can also be easily adapted for screening polymorphism such as those in HLA genes, or detecting for the presence of pathogenic RNA or DNA, or the differentiation among different strains of bacteria or viruses.

The invention will now be further illustrated by the following examples:

EXAMPLES

Detecting and identifying mutation in the Cystic Fibrosis and the Gaucher gene regions The Cystic Fibrosis (CF) gene has been cloned and the cDNA therefor has been completely sequenced. See, for example, Rommens, J. M., et al. (1989), Science 245, 1059–1065; Riordan, J. R., et al. (1989), Science 245, 1066–1073; Kerem, B., et al. (1989), Science 245, 1073–1080. The CF gene is more than 250 kb in length and encodes a transcript of about 6.5 kb in length, the transcript encoding sequences of the gene being divided amongst 27 exons. The protein encoded by the gene, i.e., translated from the aforesaid transcript, is 1480 amino units in length having a molecular weight of about 168 Kd. Due to its putative role in the regulation of ion transport across the membrane, the CF protein and hence the CF gene has also been renamed the Cystic Fibrosis transmembrane conductance regulator (CFTR protein and CFTR gene).

Since the elucidation of the complete cDNA sequence many patients suffering from Cystic Fibrosis have been tested for the presence of mutation within the CFTR gene in an attempt to understand the molecular basis of the disease. From these studies it has been observed that a deletion of three base pairs within exon No. 10, which results in the loss of a single codon, No. 508, encoding a phenylalanine residue is the most frequent mutation among Cystic Fibrosis patients and causes Cystic Fibrosis with pancreatic insufficiency. To date, more than 240 additional mutations, each of general lower frequency in the general population but in some instances a very high frequency in the studied populations, have been reported.

Similarly, the Gaucher gene has also been cloned and the cDNA therefor has been completely sequenced. See, for example Ginns et al. (1984) Biochem. Biophs. Res. Commn., 123(2), 574–580; Sorge et al. (1985) Proc. Natl. Acad. Sci. USA, 82, 7289–7293; Tsuji et al. (1986) J. Biol. Chem., 261(1), 50–53. The Gaucher gene (GCB) encodes a transcript of about 6.5 kb in length, the transcript encoding sequences of the gene being divided amongst 11 exons. The protein encoded by the gene, i.e., translated from the aforesaid transcript, is the enzyme glucocerebrosidase, a polypeptide of about 56 Kd synthesized on polysomes. Gaucher disease belongs to the large group of sphingolipidoses that are disorders in which sphingolipids are stored due to a deficiency of an enzyme required for their breakdown. Gaucher disease is the most prevalent lysosomal storage disease. World wide, an estimated 20,000 to 30,000 individuals are affected with Gaucher disease, see Grabowski et al. (1990) Biochem. Mol. Biol., 25(6), 385–414. To date, ca. 20 mutations each with characterizing frequency in the general population have been reported.

The existence of a large number of different mutations of low frequency has made it difficult to detect and identify mutations especially in Cystic Fibrosis patients. All of the aforementioned mutations were identified following the laborious procedure of isolating and sequencing CFTR or GCB alleles of Cystic Fibrosis and Gaucher patients, respectively. Accordingly, to positively diagnose a suspected Cystic Fibrosis and/or Gaucher patient and to identify the exact mutation in the CFTR and/or the GCB gene causing these conditions has up to now been an arduous process. The method of the present invention, as detailed above, overcomes difficulties encountered with prior art methods and provides a much more rapid and efficient screening procedure to determine whether the mutation occurred at various defined sites of various genes and/or individuals, simultaneously.

Table II lists eight of the most common mutations in the exons of the CFTR gene. Next to each mutation appears the specific test oligonucleotide to be used in the broad application of the present invention to detect this mutation and the labeled dideoxynucleotide which would be incorporated at the 3'-end of the specific test oligonucleotide in a normal individual and in an individual having the mutation. Also listed in Table II are three common mutations in the introns of the CFTR gene, the specific test oligonucleotides which may be used to detect and determine the mutations, and the labeled primer extension nucleotides, e.g., dideoxynucleotide, which would be incorporated at the 3'-end of the test oligonucleotides in normal or mutant individual

TABLE II

| Mutation Site | Specific oligomer primer (15-mer) | Labeled ddXTP incorporation at 3'-end of oligomer primer | | SEQ ID NO: |
|---|---|---|---|---|
| | | NORMAL | MUTANT | |
| (i) in EXONS | | | | |
| ΔF508 | 5' ATCATAGGAAACACC 3' | ddATP | ddGTP | 1 |
| ΔI507 | 5' GGAAACACCAAAGAT 3' | ddGTP | ddATP | 2 |
| 542 | 5' GTGATTCCACCTTCT 3' | ddCTP | ddTTP | 3 |
| 551 | 5' ATTCTTGCTCGTTGA 3' | ddCTP | ddTTP | 4 |
| 553 | 5' AAGAAATTCTTGCTC 3' | ddGTP | ddATP | 5 |
| 560 | 5' TCTTTGTATACTGCT 3' | ddCTP | ddGTP | 6 |
| 1282 | 5' TCCAAAGGCTTTCCT 3' | ddCTP | ddTTP | 7 |
| 1303 | 5' TTCATAGGGATCCAA 3' | ddGTP | ddCTP | 8 |
| (ii) in INTRONS | | | | |
| 621 + 1 | 5' TTGATTTATAAGAAG 3' | ddGTP | ddTTP | 9 |
| 711 + 1 | 5' AACAAATTTGATGAA 3' | ddGTP | ddTTP | 10 |
| 1717 − 1 | 5' TGCCAACTAGAAGAG 3' | ddGTP | ddATP | 11 |

It should be noted that instead of using the specific oligonucleotide primers noted in Table II above, each of which is capable of annealing with the RNA or with only one of the two DNA strands of the CFTR gene at the specific site, it is also possible, when the sample is in the form of DNA, to use an alternative primer specific for the same CFTR gene site but which is complementary to the other DNA strand, as is detailed in the preferred, more economic application of the present invention.

Table III lists nine of the most common mutations in the exons of the GCB gene causing Gaucher disease. Next to each mutation appears the specific test oligonucleotide to be used in the preferred more economic application of the present invention to detect this mutation (above), the template sequence (below) in which the underlined nucleotide base is the examined nucleotide, and the labeled dideoxynucleotide which would be incorporated at the 3'-end of the specific test oligonucleotide in an individual having the mutation.

Example 1

Figure 3:
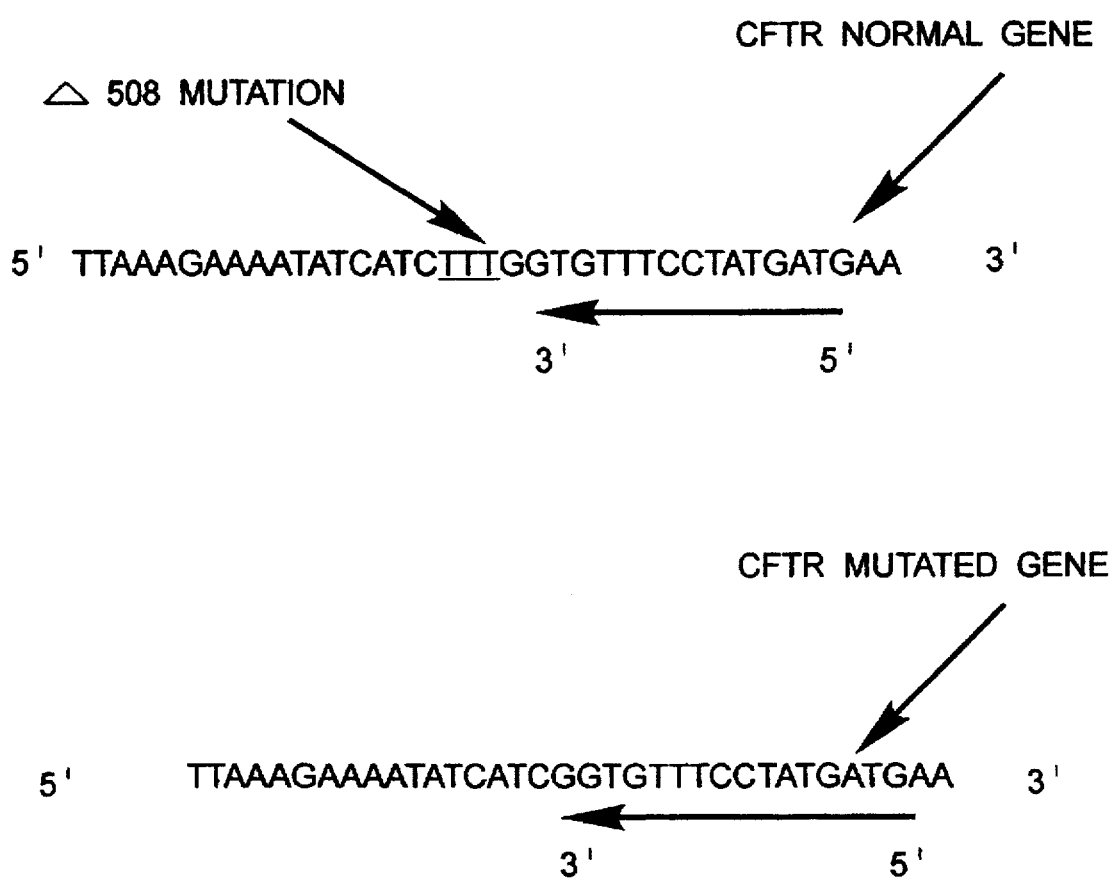
FIG. 3 is a schematic depiction of the operation of the basic method of FIG. 1 when applied to detecting a 3 bp deletion mutation in the CFTR gene.

FIG. 3 illustrates the testing of the presence of a ΔF508 mutation in a CFTR gene using the basic method. A primer (denoted as an arrow in the Figure) having the sequence 5'ATCATAGGAAACACC3' (SEQ ID NO:30) is annealed to the template DNA and then following an incorporation or extension reaction the identity of the incorporated ddXTP in the extended primer is tested. Each type of ddXTP (i.e., ddATP, ddCTP, ddGTP and ddTTP) contains a different type of detection moiety and therefore the reaction is carried out in a single vessel. The normal gene contains a T triplet (TTT) at the tested site and hence the incorporated ddXTP will be a ddATP, and in a mutated gene, where this triplet has been deleted, the incorporated ddXTP will be ddGTP. Incorporation of only ddATP will indicate a normal subject. Incorporation of only ddGTP will indicate a subject which carries two alleles of the mutated gene, i.e., homozygous. Incorporation of both ddATP and ddGTP will indicate that the subject is heterozygous for this mutation.

TABLE III

| Mutation | Substitution | Template and Primer sequence SEQ ID NOS are in brackets | Annealed Nucleotide |
|---|---|---|---|
| 84GG | insertion of G | primer CTGGCAGCCTCACAGGATTG (12) | dGTP |
| | | Template GACCGTCGGAGTGTCCTAACC (13) | |
| IVS2+1 | G→A | primer GGCAGTGTCGTGGCATCAG (14) | dATP |
| | | Template CCGTCACAGCACCCGTAGTCT (15) | |
| 370 | A→G | primer GCCT T TGT CCTTACCCTAGA (16) | dGTP |
| | | Template CGGAAACAGGAATGGGATCTC (17) | |
| 394 | G→T | primer ACGCATTGAAACAGCTGTCA (18) | dATP |
| | | Template TTGCGTAAC T TTGTCGACAGT (19) | |
| 409 | G→C | primer TGTGCAAAATGTTTGTCGGG (20) | dGTP |
| | | Template CACACGTTTTACAAACAGCCC (21) | |
| 444 | T→C | primer CCTGCGTCACCGTGACTACG (22) | dGTP |
| | | Template CGGACGCAGTGGCACTGATGC (23) | |
| 456 | G→C | primer GACAACACCAGCACGATTTG (24) | dGTP |
| | | Template CCTGTTGTGGTCGTGCTAAAC (25) | |
| 463 | C→T | primer CCACTCCCGTTACCACTCCA (26) | dATP |
| | | Template TGGTGAGGGCAATGGTGAGGT (27) | |
| 496 | G→A | primer TCACACCTACCTGTGGCGTC (28) | dATP |
| | | Template AGTGTGGATGGACACCGCAGT (29) | |

Example 2

Figure 4:
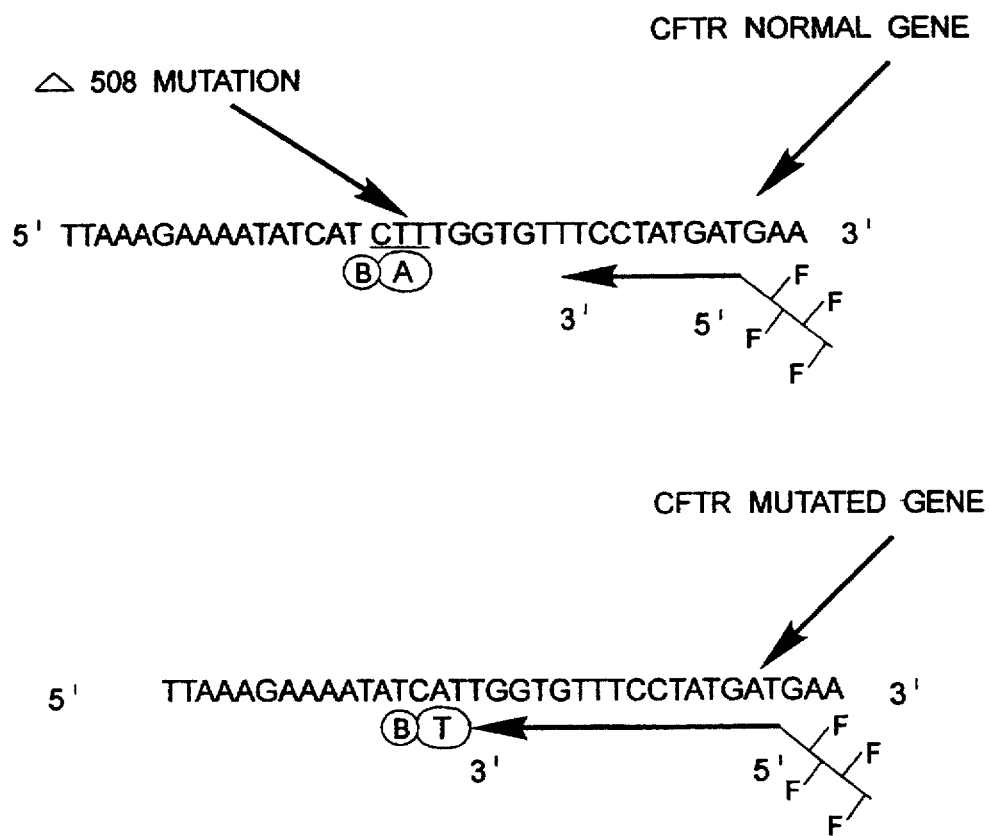
FIG. 4 is a schematic depiction of the operation of the modified method of FIG. 2 when applied to detecting a 3 bp deletion mutation in the CFTR gene.
Figure 4A:
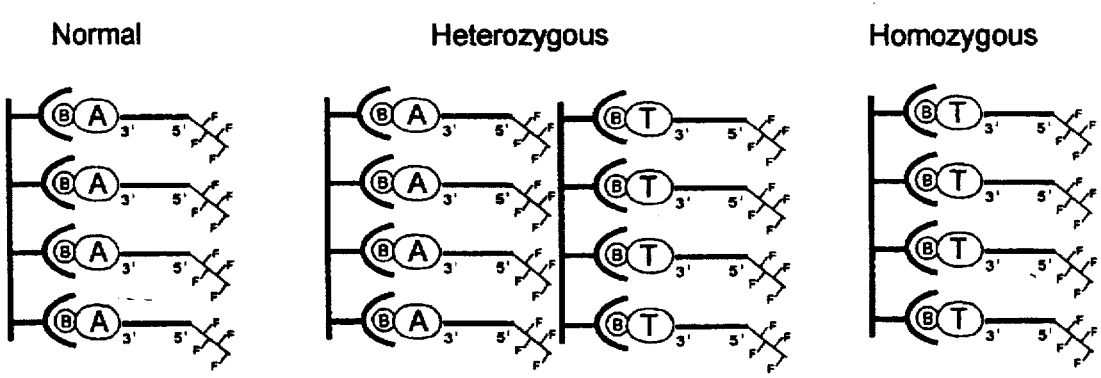

FIG. 4 illustrates use of the modified methods in the testing for the presence of the ΔF508 mutation in the CFTR gene. The reaction is performed in two different vessels. One of the vessels contains all the reaction components and biotinylated deoxynucleotide (dATP) or dideoxynucleotide (ddATP) denoted in the Figure as 'A', while the second vessel contains the reaction components but with d/ddGTP. A primer, which may be the same as used in Example 1, but 5' multi-labeled with a fluorescent marker, denoted as 'F' in the Figure, is annealed to the template DNA. Following the incorporation of the biotinylated nucleotide into the marked primer, the extended and non-extended primers are separated through the binding of the extended primers to streptavidin solid support. Thus, while the extended primer is bound to the streptavidin matrix, the non-extended primer is washed away.

Example 3

Figure 5A:
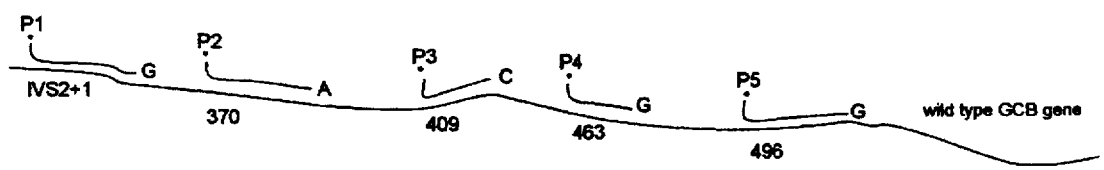
Figure 5B:
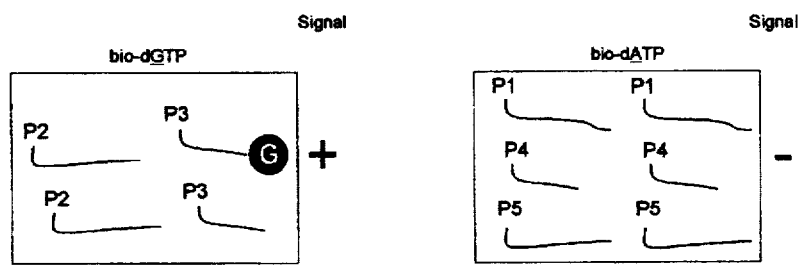
Figure 5C:
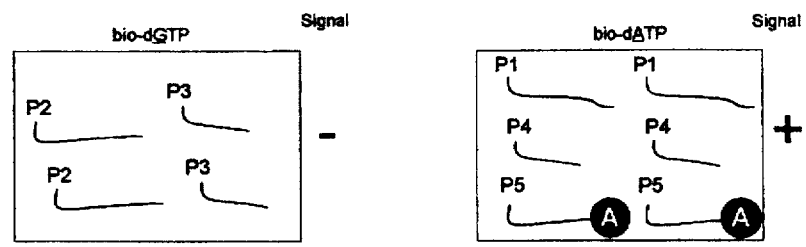
Figure 6A:
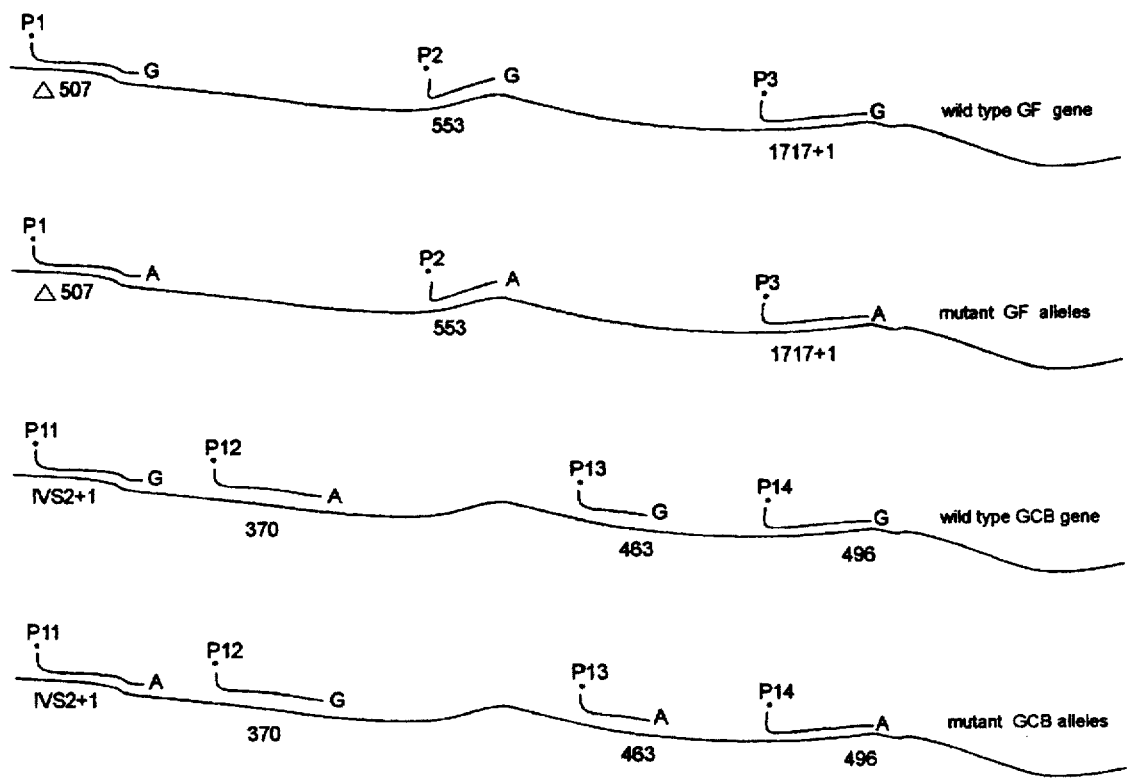
FIGS. 6A–E present a schematic depiction of the operation of the preferred embodiment for the simultaneous complete genotyping of 7 mutations, 3 of the Cystic Fibrosis gene and 4 of the Gaucher gene.
Figure 6B:
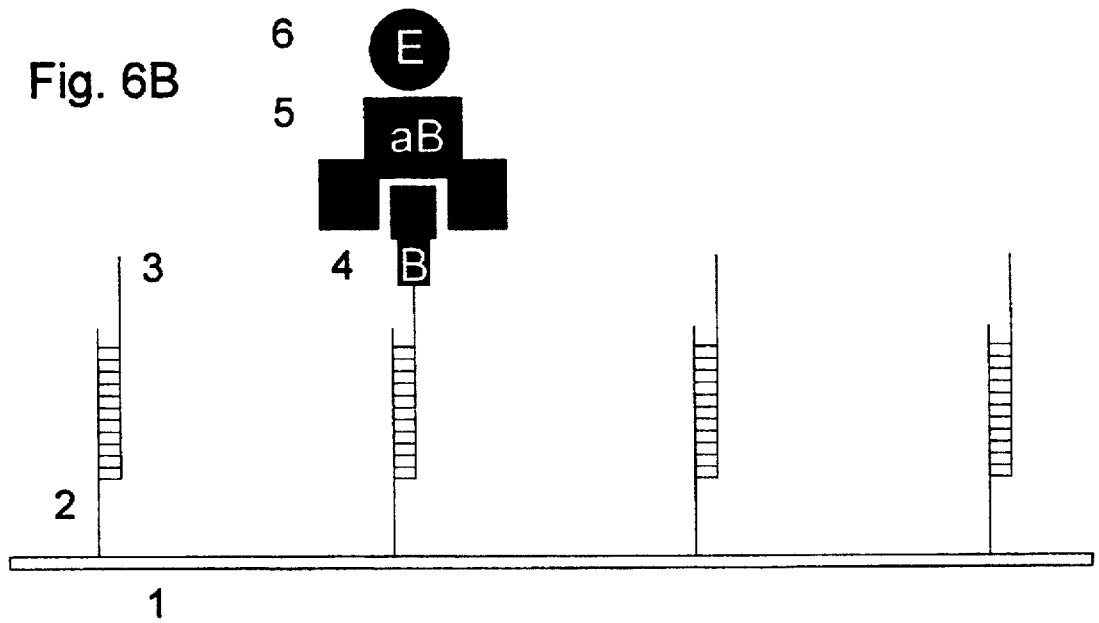
Figure 6C:
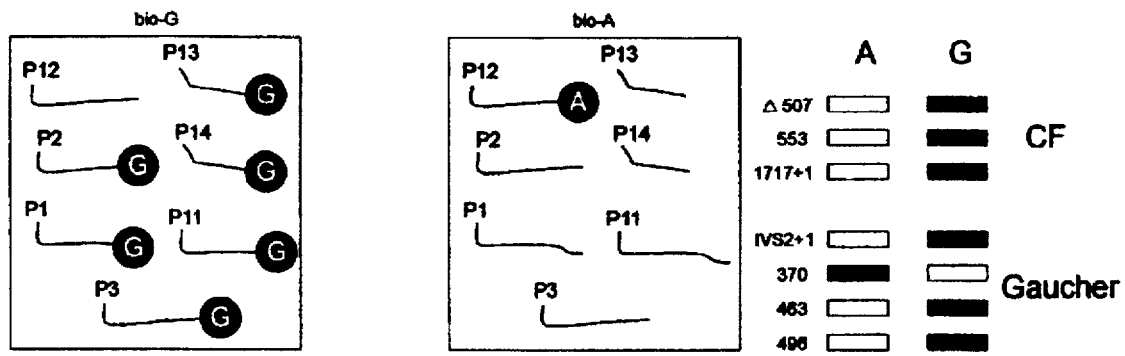
Figure 6D:
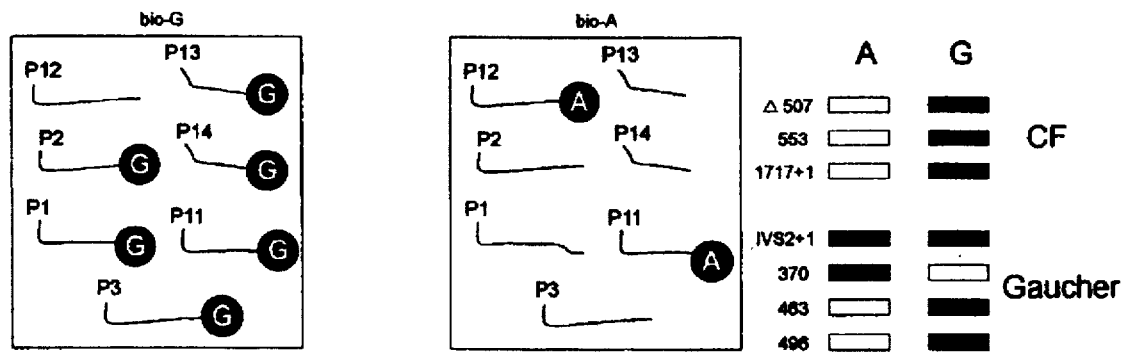
Figure 6E:
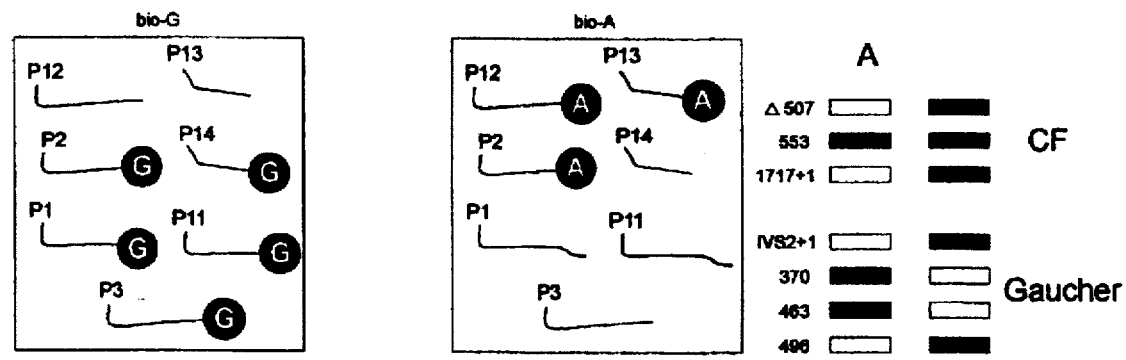
Figure 7A:
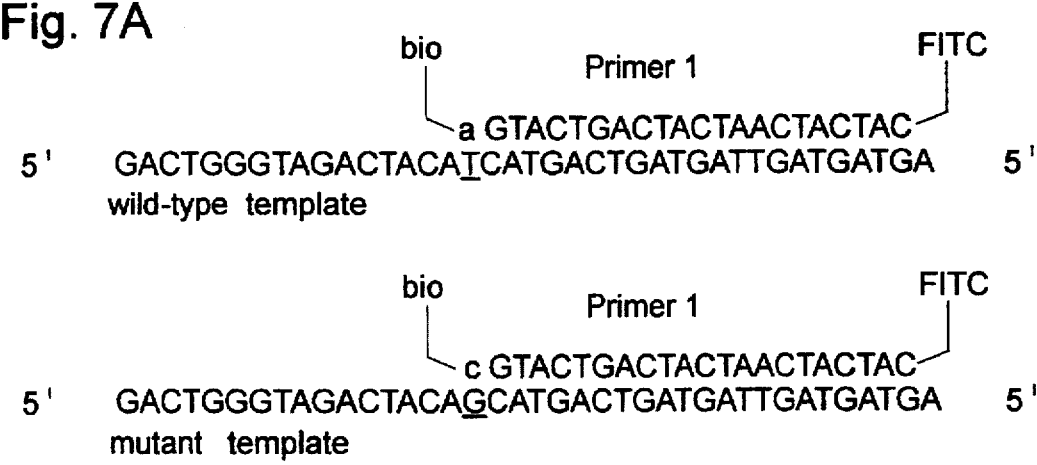
FIGS. 7A–D present a schematic depiction of the operation of the preferred embodiment for the use of one kind of a primer extension unit's extension moiety conjugated to a separation and a detection moieties for the detection of allelism in the Gaucher gene.
Figure 7B:
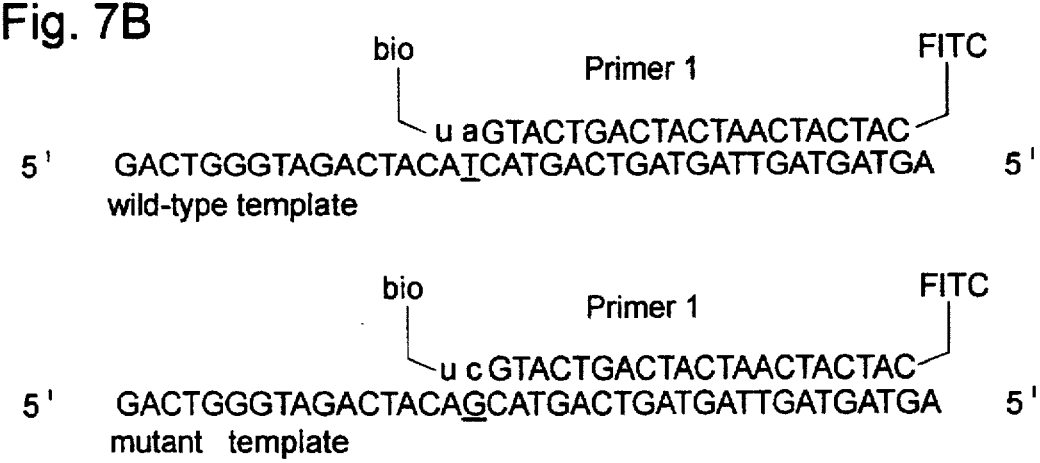
Figure 7C:
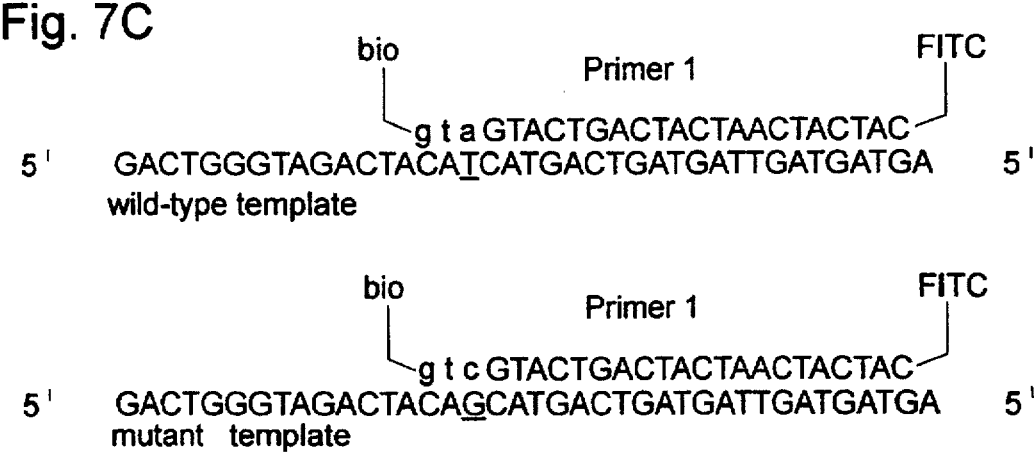
Figure 7D:
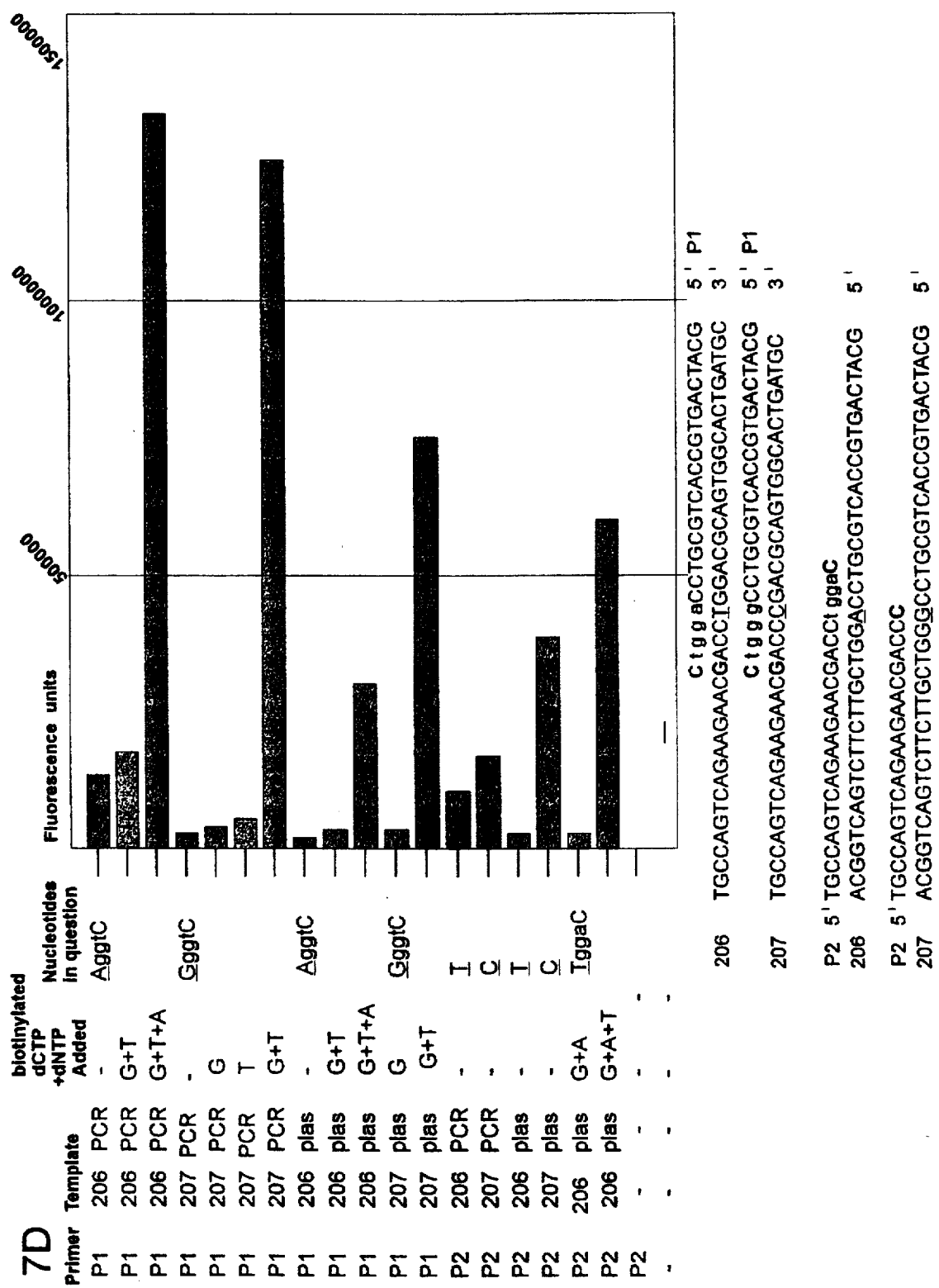

FIG. 5 illustrates use of the preferred more economic application of the preferred embodiment to simultaneously detect the presence of any of 5 GCB mutations in a carrier of the 409 mutation (G→C) and in the DNA of an individual homozygote for the 496 mutation (C→T). The reaction is performed in two different vessels for each individual. One of the vessels contains all the reaction components and biotinylated deoxynucleotide (dATP) or dideoxynucleotide (ddATP) denoted in the Figure as 'bio-dATP', while the second vessel contains the reaction components but with biotinilated d/ddGTP. Two combinations of primers are prepared. One combination contains primers P2 and P3 that will incorporate bio-dGTP provided that the examined individual is homo- or heterozygote for the 370 (T→C) and/or for the 409 GCB gene mutations. The other combination contains primers P1, P4 and P5 that will incorporate bio-dATP provided that the examined individual is homo- or heterozygote for the IVS2+1 (C→T), 463 (C→T) and/or of the 496 GCB gene mutations. The primers in each combination, which are 5' multi-labeled, are annealed, to the template DNA in a different vessel containing the relevant primer extension unit, altogether two vessels per examined individual. The extended and non-extended primers are separated through the binding of the extended primers to streptavidin solid support. Thus, while the extended primers are bound to the streptavidin matrix, the non-extended primers are washed away. Detection for the presence of extended primers via the detection moiety of the primer extension unit, or preferably the detection function of the oligonucleotides yields a positive and negative signals from the first and second primer combinations for the 409 mutation carrier and the second and first primer combinations for the individual homozygous for the 496 mutation, respectively (parts A, B and C in the Figure). Results of such experiments are delineated in part D of FIG. 5. In one type of experiment the presence or absence of any of two sequence alterations (IVS2+1 and V394L) of the Gaucher gene was determined for six independent individuals (first six rows of the table) of predetermined genotype out of which positive signal, that is the examined individual is carrying at least one of the mutations in at least heterozygote form, was obtained only from an individual who is heterozygote for the IVS2+1 mutation. Any of the other five examined individuals, who are not carriers of the above mutations did not show positive signal and are therefore defined as "Normal". In a second type of experiment the presence or absence of any of four sequence alterations (84GG, N370S, D409H and L444P) of the Gaucher gene was determined for five independent individuals of predetermined genotype (last five rows in the table) out of which a positive signal, that is the examined individual is carrying at least one of the mutations in at least heterozygote form, was obtained for four of the examined individuals in full agreement with their predetermined genotype.

Example 4

FIG. 6 illustrates use of the preferred embodiment to simultaneously detect and identify 7 mutations, 3 of the CFTR gene and 4 of the GCB gene in two reaction vessels. One of the vessels contains all the reaction components and biotinylated deoxynucleotide (dATP), or dideoxynucleotide (ddATP), denoted in the Figure as 'bio-A', while the second vessel contains the reaction components but with biotinylated d/ddGTP. The primers, which are 5' multi-labeled, are pooled and are then annealed to the examined DNA templates in the two independent vessels, each containing a different primer extension unit. The extended and non-extended primers are separated through the binding of the extended primers to streptavidin solid support. Thus, while the extended primers are bound to the streptavidin matrix, the non-extended primers are washed away. A sample of pre-separated primers or preferably the extended primers, eluted from the solid support are sorted via the separation function of the oligonucleotides by hybridization to complementary oligonucleotides adhered to a test surface, as shown in part B of the Figure. Detection for the presence of extended primers via the detection function of the oligonucleotides, or preferably, the detection moiety of the primer extension unit, as shown in the Figure using enzyme marker conjugated antibiotin (denoted as E-αB in part B of the Figure) yields positive (dark boxes in parts C, D and E of the Figure) and negative (open boxes) signals enabling the simultaneous complete genotyping of an individual regarding the examined DNA sequences. Such analysis of a normal individual; of a carrier i.e., heterozygous for the GCB IVS2+1 mutation; and of an individual who is a carrier of the CFTR 553 mutation and is homozygous for the GCB 463 mutation, is presented in parts C, D and E of the Figure, respectively.

Example 5

FIG. 7 illustrates use of the preferred embodiment in detecting specific sequence alterations using one type of primer extension unit's extension moiety conjugated to a separation and a detection moieties for the detection of allelism in the GCB gene. Consider allelism caused by a T→G mutation (underlined) in DNA templates (bottom sequences). An oligonucleotide primer having a sequence which is complementary to the sequence of the region 3' of and immediately flanking the 3'-end of the suspected mutation site (upper sequence) is annealed to the template DNA and two primer extension reactions, each including a different biotin conjugated (denoted as 'bio' in the Figure) primer extension unit, capable of base pairing with the two alternating nucleotide bases in the examined site of allelism (part A of the Figure). Extension of the oligonucleotide primer by one primer extension unit will occur provided that the unit is complementary to the examined nucleotide. A different approach, as depicted in B and C in the Figure, enables the use of one type of biotin conjugated primer extension unit (biotin-d/ddUTP or biotin-d/ddGTP in part B or C of the Figure, respectively), capable of base pairing with the first (in part B) or second (in part C) nucleotide base following the examined nucleotide base in the direction of synthesis. In this approach the differentiating nucleotides are primer extension units capable of base pairing with the examined nucleotide base, devoid of separation and detection moieties and enabling further extension in the direction of synthesis. In the given example the differentiating nucleotides are dATP and dCTP. Part B of the Figure demonstrates the extension of the primer by two primer extension units whereas in part C a third primer extension unit (dTTP) devoid of separation and detection moieties and enabling further extension in the direction of synthesis is used, leading to extension of the primer by four primer extension units of which only the third to be added contains a separation and detection moieties. Such analysis aimed at identifying two DNA sequences differentiating in one nucleotide base (designated 206 and 207 in part D of the Figure) using two different oligonucleotide primers (P 1 and P2) each capable of annealing with a different strand of the examined DNA and is having a sequence which is complementary to the sequence of the region 3' of and immediately flanking the 3'-end of the mutation site. Presented is the use of different combinations of primer extension units, common to all is the use of dCTP-biotin as the primer extension unit harboring separation and detection moieties.

Example 6

A diagnostic kit for screening or detecting mutations

A diagnostic kit for carrying out a preferred embodiment of the methods according to the present invention detailed above may contain the following constituents:

a) combinations of one or more marked oligonucleotide primers, each primer in the combination designed to be specific for a particular gene or region in a gene;

b) one or more primer extension units, each including a deoxyribonucleotide or a dideoxynucleotide serving as the extension moiety and further including biotin serving as the separation and detection moieties;

c) suitable buffer/s in aqueous solution for carrying out the annealing, extension, binding wash and separative-affinity/hybridization steps of the method;

d) a suitable template dependent extension enzyme for carrying out the primer extension unit incorporation, or extension, step of the method; and e) solid supports one for effecting the separation between extended and non-extended primers, the other, preferably a test surface, for the assortment of different extended primers.

When the kit is to be used for CFTR and Gaucher gene screening, it may contain any one or all of the specific oligonucleotide primers listed in Tables II and III above for screening or detecting the most common mutations occurring in these genes. When the kit is to be used in the screening for the presence of one or all of the various known generic diseases, e.g., those listed in Table I above, it may contain any suitable number of the specific or pooled oligonucleotide primers in any suitable combination for screening for mutations in particular disease related genes. In cases where a particular disease related gene may have one or more mutations, e.g., the CFTR gene, the kit should contain the specific oligonucleotide primers for screening the more common of the mutations, which may be different for different intended populations. When the kit is to be used for blood or tissue typing analysis it may contain any combination of specific oligonucleotide primers, each designed to identify a particular blood or tissue type. Depending on the circumstances, all of the kits may also contain an additional oligonucleotide primer for determining the presence or absence of a DNA sequence corresponding specifically to the presence of a pathogen, for example, the presence of the AIDS virus or a specific strata of such virus, e.g., HIV-I, HIV-II or HIV-III. Accordingly, one kit may be used for testing any number of genes or gene sites within a single gene, and this only requires that the kit contain a number of the specific oligonucleotide primers, all the other components of the kit being the same in all cases.

While the invention has been described with respect to a limited number of embodiments, it will be appreciated that many variations, modifications and other applications of the invention may be made.

---

What is claimed is:

1. A method of determining the identity of a nucleotide base at a specific position in a nucleic acid of interest, which can be used to detect point mutations, allelism, and the genotype of an examined individual, comprising the steps of:

(a) if the nucleic acid of interest is double stranded, treating said double stranded nucleic acid to obtain single stranded nucleotide bases spanning the specific position, or, if the nucleic acid of interest is single stranded, directly employing step (b);

(b) contacting said single stranded nucleotide bases spanning the specific position with an oligonucleotide primer having a 3'-end, said primer being for hybridizing with single stranded stretches of nucleotide bases present in the nucleic acid of interest adjacent the nucleotide base to be identified, so as to form a duplex between the primer and the nucleic acid of interest;

(c) contacting, in the presence of a template dependent extension enzyme, said duplex with:
 (i) a primer extension unit, said primer extension unit including an extension moiety for specifically halting a nucleic acid template dependent primer extension reaction, in a manner which is strictly dependent on the identity of an unpaired nucleotide base of the nucleic acid of interest located within the nucleic acid of interest 5' to the specific position, for permitting base pairing of said extension moiety of said primer extension unit with said unpaired nucleotide base, said oligonucleotide primer and said primer extension unit are selected such that any nucleotide bases of the nucleic acid of interest present between said 3'-end of said oligonucleotide primer and said unpaired nucleotide base are different from said unpaired nucleotide base; and
 (ii) one to three additional primer extension units, each of said one to three additional primer extension units having an extension moiety permitting primer extension, said one to three additional primer extension units are selected such that each is complementary to at least one of said nucleotide bases of the nucleic acid of interest present between said 3'-end of said oligonucleotide primer and said unpaired nucleotide base, among which at least the nucleotide base at the specific position being present;
 such that said template dependent primer extension reaction is initiated by incorporation of said one to three additional primer extension units and is halted by incorporation of said primer extension unit which has said extension moiety for specifically halting said nucleic acid template dependent primer extension reaction; and
(d) determining the presence of an extended primer.

2. A method as in claim 1, wherein said extension moiety of said primer extension unit is by itself not sufficient for halting said primer extension reaction, said primer extension reaction is halted by limiting said one to three additional primer extension units to one to two additional primer extension units.

3. A method as in claim 1, wherein said extension moiety of said primer extension unit is by itself sufficient for halting said primer extension reaction.

4. A method as in claim 1, wherein said oligonucleotide primer includes a detection group for facilitating said determination of said presence of said extended primer.

5. A method as in claim 1, wherein said primer extension unit which includes said extension moiety, itself for specifically halting said nucleic acid template dependent primer extension reaction, further includes a separation moiety for permitting affinity separation of said extended primer from non-extended primers.

6. A method as in claim 1, wherein following step (c) an additional step of cycling the reaction, is provided, by repeatedly exposing the reaction to
 (a) a denaturing condition under which said extended primer is separated from the nucleic acid of interest; followed by
 (b) a condition permitting said template dependent primer extension reaction to take place.

7. A method as in claim 1, wherein said 3'-end of said oligonucleotide primer is located immediately adjacent to, and 3' of the nucleotide base at the specific position, such that no nucleotide bases are present within the nucleic acid of interest between said 3'-end of said primer and said specific position.

* * * * *

SEQUENCE LISTING ( 1 ) GENERAL INFORMATION:

( i i i ) NUMBER OF SEQUENCES:50

( 2 ) INFORMATION FOR SEQ ID NO:1:

( i ) SEQUENCE CHARACTERISTICS:
( A ) LENGTH:15
( B ) TYPE:nucleic acid
( C ) STRANDEDNESS:single
( D ) TOPOLOGY:linear ( x i ) SEQUENCE DESCRIPTION: SEQ ID NO:1:

ATCATAGGAA ACACC 15

( 2 ) INFORMATION FOR SEQ ID NO:2:

( i ) SEQUENCE CHARACTERISTICS:
( A ) LENGTH:15
( B ) TYPE:nucleic acid
( C ) STRANDEDNESS:single
( D ) TOPOLOGY:linear ( x i ) SEQUENCE DESCRIPTION: SEQ ID NO:2:

GGAAACACCA AAGAT 15

( 2 ) INFORMATION FOR SEQ ID NO:3:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:3:

GTGATTCCAC CTTCT 15

( 2 ) INFORMATION FOR SEQ ID NO:4:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:4:

ATTCTTGCTC GTTGA 15

( 2 ) INFORMATION FOR SEQ ID NO:5:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:5:

AAGAAATTCT TGCTC 15

( 2 ) INFORMATION FOR SEQ ID NO:6:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:6:

TCTTTGTATA CTGCT 15

( 2 ) INFORMATION FOR SEQ ID NO:7:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:7:

TCCAAAGGCT TTCCT 15

( 2 ) INFORMATION FOR SEQ ID NO:8:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:8:

TTCATAGGGA TCCAA 15

( 2 ) INFORMATION FOR SEQ ID NO:9:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:9:

TTGATTTATA AGAAG 15

( 2 ) INFORMATION FOR SEQ ID NO:10:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:10:

AACAAATTTG ATGAA 15

( 2 ) INFORMATION FOR SEQ ID NO:11:

( i ) SEQUENCE CHARACTERISTICS:
        ( A ) LENGTH:15
        ( B ) TYPE:nucleic acid
        ( C ) STRANDEDNESS:single
        ( D ) TOPOLOGY:linear ( x i ) SEQUENCE DESCRIPTION: SEQ ID NO:11:

TGCCAACTAG AAGAG 15

( 2 ) INFORMATION FOR SEQ ID NO:12:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:12:

CTGGCAGCCT CACAGGATTG 20

( 2 ) INFORMATION FOR SEQ ID NO:13:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:13:

CCAATCCTGT GAGGCTGCCA G 21

( 2 ) INFORMATION FOR SEQ ID NO:14:

( i ) SEQUENCE CHARACTERISTICS:
        ( A ) LENGTH:19
        ( B ) TYPE:nucleic acid
        ( C ) STRANDEDNESS:single
        ( D ) TOPOLOGY:linear ( x i ) SEQUENCE DESCRIPTION: SEQ ID NO:14:

GGCAGTGTCG TGGCATCAG 19

( 2 ) INFORMATION FOR SEQ ID NO:15:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:15:

TCTGATGCCC ACGACACTGC C 21

( 2 ) INFORMATION FOR SEQ ID NO:16:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:16:

GCCTTTGTCC TTACCCTAGA 20

( 2 ) INFORMATION FOR SEQ ID NO:17:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:17:

CTCTAGGGTA AGGACAAAGG C 21

( 2 ) INFORMATION FOR SEQ ID NO:18:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:18:

ACTGTCGACA AAGTTACGCA 20

( 2 ) INFORMATION FOR SEQ ID NO:19:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:19:

TTGCGTAACT TTGTCGACAG T 21

( 2 ) INFORMATION FOR SEQ ID NO:20:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:20:

GGGCTGTTTG TAAAACGTGT 20

( 2 ) INFORMATION FOR SEQ ID NO:21:

( i ) SEQUENCE CHARACTERISTICS:
    ( A ) LENGTH:21
    ( B ) TYPE:nucleic acid
    ( C ) STRANDEDNESS:single
    ( D ) TOPOLOGY:linear ( x i ) SEQUENCE DESCRIPTION: SEQ ID NO:21:

CACACGTTTT ACAAACAGCC C 21

( 2 ) INFORMATION FOR SEQ ID NO:22:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:22:

GCATCAGTGC CACTGCGTCC 20

( 2 ) INFORMATION FOR SEQ ID NO:23:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:23:

CGGACGCAGT GGCACTGATG C 21

( 2 ) INFORMATION FOR SEQ ID NO:24:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:24:

GTTTAGCACG ACCACAACAG 20

( 2 ) INFORMATION FOR SEQ ID NO:25:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:25:

CCTGTTGTGG TCGTGCTAAA C 21

( 2 ) INFORMATION FOR SEQ ID NO:26:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( x i ) SEQUENCE DESCRIPTION: SEQ ID NO:26:

ACCTCACCAT TGCCCTCACC 20

( 2 ) INFORMATION FOR SEQ ID NO:27:

( i ) SEQUENCE CHARACTERISTICS:

(A) LENGTH:21
                (B) TYPE:nucleic acid
                (C) STRANDEDNESS:single
                (D) TOPOLOGY:linear (x i) SEQUENCE DESCRIPTION: SEQ ID NO:27:

TGGTGAGGGC AATGGTGAGG T 21

(2) INFORMATION FOR SEQ ID NO:28:

(i) SEQUENCE CHARACTERISTICS:
                (A) LENGTH:20
                (B) TYPE:nucleic acid
                (C) STRANDEDNESS:single
                (D) TOPOLOGY:linear (x i) SEQUENCE DESCRIPTION: SEQ ID NO:28:

TCACACCTAC CTGTGGCGTC 20

(2) INFORMATION FOR SEQ ID NO:29:

(i) SEQUENCE CHARACTERISTICS:
                (A) LENGTH:21
                (B) TYPE:nucleic acid
                (C) STRANDEDNESS:single
                (D) TOPOLOGY:linear (x i) SEQUENCE DESCRIPTION: SEQ ID NO:29:

TGACGCCACA GGTAGGTGTG A 21

(2) INFORMATION FOR SEQ ID NO:30:

(i) SEQUENCE CHARACTERISTICS:
                (A) LENGTH:15
                (B) TYPE:nucleic acid
                (C) STRANDEDNESS:single
                (D) TOPOLOGY:linear (x i) SEQUENCE DESCRIPTION: SEQ ID NO:30:

ATCATAGGAA ACACC 15

(2) INFORMATION FOR SEQ ID NO:31:

(i) SEQUENCE CHARACTERISTICS:
                (A) LENGTH:38
                (B) TYPE:nucleic acid
                (C) STRANDEDNESS:single
                (D) TOPOLOGY:linear (x i) SEQUENCE DESCRIPTION: SEQ ID NO:31:

TTAAAGAAAA TATCATCTTT GGTGTTTCCT ATGATGAA 38

(2) INFORMATION FOR SEQ ID NO:32:

(i) SEQUENCE CHARACTERISTICS:
                (A) LENGTH:38
                (B) TYPE:nucleic acid
                (C) STRANDEDNESS:single
                (D) TOPOLOGY:linear (x i) SEQUENCE DESCRIPTION: SEQ ID NO:32:

TTAAAGAAAA TATCATCATC GGTGTTTCCT ATGATGAA 38

(2) INFORMATION FOR SEQ ID NO:33:

(i) SEQUENCE CHARACTERISTICS:
                (A) LENGTH:38
                (B) TYPE:nucleic acid (C) STRANDEDNESS:single
(D) TOPOLOGY:linear (xi) SEQUENCE DESCRIPTION: SEQ ID NO:33:

TTAAAGAAAA TATCATCTTT GGTGTTTCCT ATGATGAA  38

(2) INFORMATION FOR SEQ ID NO:34:

(i) SEQUENCE CHARACTERISTICS:
      (A) LENGTH:35
      (B) TYPE:nucleic acid
      (C) STRANDEDNESS:single
      (D) TOPOLOGY:linear (xi) SEQUENCE DESCRIPTION: SEQ ID NO:34:

TTAAAGAAAA TATCATTGGT GTTCCTATG ATGAA  35

(2) INFORMATION FOR SEQ ID NO:35:

(i) SEQUENCE CHARACTERISTICS:
      (A) LENGTH:42
      (B) TYPE:nucleic acid
      (C) STRANDEDNESS:single
      (D) TOPOLOGY:linear (xi) SEQUENCE DESCRIPTION: SEQ ID NO:35:

GACTGGGTAG ACTACATCAT GACTGATGAT TGATGATGAT GA  42

(2) INFORMATION FOR SEQ ID NO:36:

(i) SEQUENCE CHARACTERISTICS:
      (A) LENGTH:42
      (B) TYPE:nucleic acid
      (C) STRANDEDNESS:single
      (D) TOPOLOGY:linear (xi) SEQUENCE DESCRIPTION: SEQ ID NO:36:

GACTGGGTAG ACTACAGCAT GACTGATGAT TGATGATGAT GA  42

(2) INFORMATION FOR SEQ ID NO:37:

(i) SEQUENCE CHARACTERISTICS:
      (A) LENGTH:22
      (B) TYPE:nucleic acid
      (C) STRANDEDNESS:single
      (D) TOPOLOGY:linear (xi) SEQUENCE DESCRIPTION: SEQ ID NO:37:

CATCATCAAT CATCAGTCAT GA  22

(2) INFORMATION FOR SEQ ID NO:38:

(i) SEQUENCE CHARACTERISTICS:
      (A) LENGTH:22
      (B) TYPE:nucleic acid
      (C) STRANDEDNESS:single
      (D) TOPOLOGY:linear (xi) SEQUENCE DESCRIPTION: SEQ ID NO:38:

CATCATCAAT CATCAGTCAT GC  22

(2) INFORMATION FOR SEQ ID NO:39:

(i) SEQUENCE CHARACTERISTICS:
      (A) LENGTH:23
      (B) TYPE:nucleic acid
      (C) STRANDEDNESS:single
      (D) TOPOLOGY:linear ( x i ) SEQUENCE DESCRIPTION: SEQ ID NO:39:

CATCATCAAT CATCAGTCAT GAU  23

( 2 ) INFORMATION FOR SEQ ID NO:40:

( i ) SEQUENCE CHARACTERISTICS:
        ( A ) LENGTH:23
        ( B ) TYPE:nucleic acid
        ( C ) STRANDEDNESS:single
        ( D ) TOPOLOGY:linear ( x i ) SEQUENCE DESCRIPTION: SEQ ID NO:40:

CATCATCAAT CATCAGTCAT GCU  23

( 2 ) INFORMATION FOR SEQ ID NO:41:

( i ) SEQUENCE CHARACTERISTICS:
        ( A ) LENGTH:24
        ( B ) TYPE:nucleic acid
        ( C ) STRANDEDNESS:single
        ( D ) TOPOLOGY:linear ( x i ) SEQUENCE DESCRIPTION: SEQ ID NO:41:

CATCATCAAT CATCAGTCAT GATG  24

( 2 ) INFORMATION FOR SEQ ID NO:42:

( i ) SEQUENCE CHARACTERISTICS:
        ( A ) LENGTH:24
        ( B ) TYPE:nucleic acid
        ( C ) STRANDEDNESS:single
        ( D ) TOPOLOGY:linear ( x i ) SEQUENCE DESCRIPTION: SEQ ID NO:42:

CATCATCAAT CATCAGTCAT GCTG  24

( 2 ) INFORMATION FOR SEQ ID NO:43:

( i ) SEQUENCE CHARACTERISTICS:
        ( A ) LENGTH:25
        ( B ) TYPE:nucleic acid
        ( C ) STRANDEDNESS:single
        ( D ) TOPOLOGY:linear ( x i ) SEQUENCE DESCRIPTION: SEQ ID NO:43:

GCATCAGTGC CACTGCGTCC AGGTC  25

( 2 ) INFORMATION FOR SEQ ID NO:44:

( i ) SEQUENCE CHARACTERISTICS:
        ( A ) LENGTH:41
        ( B ) TYPE:nucleic acid
        ( C ) STRANDEDNESS:single
        ( D ) TOPOLOGY:linear ( x i ) SEQUENCE DESCRIPTION: SEQ ID NO:44:

TGCCAGTCAG AAGAACGACC TGGACGCAGT GGCACTGATG C  41

( 2 ) INFORMATION FOR SEQ ID NO:45:

( i ) SEQUENCE CHARACTERISTICS:
        ( A ) LENGTH:25
        ( B ) TYPE:nucleic acid
        ( C ) STRANDEDNESS:single
        ( D ) TOPOLOGY:linear ( x i ) SEQUENCE DESCRIPTION: SEQ ID NO:45:

```
GCATCAGTGC  CACTGCGTCC  GGGTC                                    25
```

( 2 ) INFORMATION FOR SEQ ID NO:46:

( i ) SEQUENCE CHARACTERISTICS:
        ( A ) LENGTH:41
        ( B ) TYPE:nucleic acid
        ( C ) STRANDEDNESS:single
        ( D ) TOPOLOGY:linear ( x i ) SEQUENCE DESCRIPTION: SEQ ID NO:46:

```
TGCCAGTCAG  AAGAACGACC  CGGACGCAGT  GGCACTGATG  C           41
```

( 2 ) INFORMATION FOR SEQ ID NO:47:

( i ) SEQUENCE CHARACTERISTICS:
        ( A ) LENGTH:25
        ( B ) TYPE:nucleic acid
        ( C ) STRANDEDNESS:single
        ( D ) TOPOLOGY:linear ( x i ) SEQUENCE DESCRIPTION: SEQ ID NO:47:

```
TGCCAGTCAG  AAGAACGACC  TGGAC                                    25
```

( 2 ) INFORMATION FOR SEQ ID NO:48:

( i ) SEQUENCE CHARACTERISTICS:
        ( A ) LENGTH:41
        ( B ) TYPE:nucleic acid
        ( C ) STRANDEDNESS:single
        ( D ) TOPOLOGY:linear ( x i ) SEQUENCE DESCRIPTION: SEQ ID NO:48:

```
GCATCAGTGC  CACTGCGTCC  AGGTCGTTCT  TCTGACTGGA  C           41
```

( 2 ) INFORMATION FOR SEQ ID NO:49:

( i ) SEQUENCE CHARACTERISTICS:
        ( A ) LENGTH:21
        ( B ) TYPE:nucleic acid
        ( C ) STRANDEDNESS:single
        ( D ) TOPOLOGY:linear ( x i ) SEQUENCE DESCRIPTION: SEQ ID NO:49:

```
TGCCAGTCAG  AAGAACGACC  C                                        21
```

( 2 ) INFORMATION FOR SEQ ID NO:50:

( i ) SEQUENCE CHARACTERISTICS:
        ( A ) LENGTH:41
        ( B ) TYPE:nucleic acid
        ( C ) STRANDEDNESS:single
        ( D ) TOPOLOGY:linear ( x i ) SEQUENCE DESCRIPTION: SEQ ID NO:50:

```
GCATCAGTGC  CACTGCGTCC  GGGTCGTTCT  TCTGACTGGA  C           41
```